United States Patent
Bernoud et al.

(10) Patent No.: US 10,245,220 B2
(45) Date of Patent: Apr. 2, 2019

(54) PROCESS FOR PONGAMOL ENRICHMENT OF KARANJA OIL

(71) Applicant: BIOSYNTHIS, Saint Cyr Sous Dourdan (FR)

(72) Inventors: Thierry Bernoud, Saint Cyr Sous Dourdan (FR); Antoine Piccirilli, Poitiers (FR); Julien Magne, Les Roches Premarie (FR)

(73) Assignee: BIOSYNTHIS, Saint Cyr Sous Dourdan (FR)

( * ) Notice: Subject to any disclaimer, the term of this patent is extended or adjusted under 35 U.S.C. 154(b) by 0 days.

(21) Appl. No.: 15/746,522

(22) PCT Filed: Jul. 22, 2016

(86) PCT No.: PCT/EP2016/067600
§ 371 (c)(1),
(2) Date: Feb. 13, 2018

(87) PCT Pub. No.: WO2017/013264
PCT Pub. Date: Jan. 26, 2017

(65) Prior Publication Data
US 2018/0207070 A1    Jul. 26, 2018

(30) Foreign Application Priority Data

Jul. 22, 2015   (FR) ..................................... 15 56973

(51) Int. Cl.
| | |
|---|---|
| *A61K 8/37* | (2006.01) |
| *A61K 8/49* | (2006.01) |
| *A61K 8/97* | (2017.01) |
| *A61Q 17/04* | (2006.01) |
| *A61Q 19/08* | (2006.01) |
| *A61K 36/486* | (2006.01) |
| *A61K 8/9789* | (2017.01) |

(52) U.S. Cl.
CPC ............... *A61K 8/37* (2013.01); *A61K 8/498* (2013.01); *A61K 8/4973* (2013.01); *A61K 8/97* (2013.01); *A61K 8/9789* (2017.08); *A61K 36/486* (2013.01); *A61Q 17/04* (2013.01); *A61Q 19/08* (2013.01)

(58) Field of Classification Search
None
See application file for complete search history.

(56) References Cited

U.S. PATENT DOCUMENTS

| | | |
|---|---|---|
| 5,152,983 A | 10/1992 | Nambudiry et al. |
| 2003/0031635 A1 | 2/2003 | Lege et al. |
| 2005/0244441 A1 | 11/2005 | Courtois et al. |
| 2016/0108013 A1 | 4/2016 | Piccirilli |

FOREIGN PATENT DOCUMENTS

| | | |
|---|---|---|
| EP | 0 514 067 A1 | 11/1992 |
| EP | 0 521 651 A2 | 1/1993 |
| EP | 0 568 307 A1 | 11/1993 |
| EP | 2 201 928 A2 | 6/2010 |
| FR | 2 720 643 A1 | 12/1995 |
| FR | 2 806 080 A1 | 9/2001 |
| FR | 2 762 008 B1 | 8/2003 |
| FR | 2 961 207 A1 | 12/2011 |
| GB | 2 237 805 A | 5/1991 |
| WO | 98/48768 A1 | 11/1998 |
| WO | 98/50005 A1 | 11/1998 |
| WO | 2008/070368 A2 | 6/2008 |
| WO | 2008/134712 A2 | 11/2008 |
| WO | 2012/041632 A1 | 4/2012 |
| WO | 2012/119861 A2 | 9/2012 |
| WO | 2014/016349 A1 | 1/2014 |
| WO | 2014/114888 A2 | 7/2014 |
| WO | 2014/195637 A1 | 12/2014 |
| WO | 2014/195638 A1 | 12/2014 |
| WO | 2014/195639 A1 | 12/2014 |

OTHER PUBLICATIONS

DSM PARSOL, 1789, Factsheet.
Givaudan Leading Sensory Innovation, Pongamia Extract & Karanja Oil, Plant actives for natural UV and antioxidant protection, Issue 4, Apr. 2008.
Sigma-Aldrich, Sébaçate de diéthyle (Diethyl sebacate) (technical document) with English translation, version 6.1.
Damiani et al., "Changes in ultraviolet absorbance and hence in protective efficacy against lipid peroxidation of organic sunscreens after UVA irradiation," Journal of Photochemistry and Photobiology B: Biology, 82, 2006.
Lim & Draelos, "Clinical Guide to Sunscreens and Photoprotection," New York, London : Informa Healthcare, 322 p.—978-1-4200-8084-1, 2009.
Exhibitors Suppliers Day—USA, May 1, 2013, pp. 1-16.
Mintel, "SPF 40 Sun Cream for th Face" GNPD, Sep. 2, 2008.
Alkyl Esters Supplement Book 2 p 54 CIR Abstract.
Sep. 14, 2016 International Search Report issued in International Application No. PCT/EP2016/067600.
Sep. 14, 2016 Written Opinion of the International Searching Authority issued in International Application No. PCT/EP2016/067600.

*Primary Examiner* — Michael Barker
(74) *Attorney, Agent, or Firm* — Oliff PLC

(57) ABSTRACT

A cosmetic ingredient, that consists of a solution of at least one extract of karanja oil including pongamol (CAS 484-33-3) and karanjin (CAS 521-88-0) in at least one solvent selected from the group of the diesters having the following formula (I), or mixtures thereof:

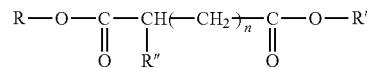

In which: n is from 0 to 19; R and R', which may be identical or different, are alkyls derived from an esterification by a linear or branched alcohol of molecular formula $C_xH_{2x+2}O$, x being from 1 to 30, from 1 to 20, and from 1 to 10. "R" is either a hydrogen atom or a $C_1$-$C_3$ alkyl group, which also relates to a process of selective precipitation, to a cosmetic formulation and also to the uses thereof.

16 Claims, 3 Drawing Sheets

PROCESS FOR PONGAMOL ENRICHMENT OF KARANJA OIL

The present invention relates to the field of oleochemistry and, more particularly, to the field of oils used in cosmetics.

More particularly, the invention relates to a process for selective extraction of unsaponifiables from a lipid material of plant origin, this renewable lipid material being karanja oil At the end of said process, an extract is obtained, said extract (consisting of a solution) being capable of being incorporated in cosmetic or pharmaceutical compositions.

Karanja is a plant of the legume family, originating in Asia. In particular, it is present in India, in Japan, and in South China. It is a tree or a robust liana measuring 20 to 30 m.

In the sense of the present application, the term "karanja" designates, in particular, the following species: *Pongamia glabra, Pongamia pinnata, Milletia pinnata, Derris indica, Gadelupa pinnata, Pongamia grandifolia, Robinia mitis, Tephrosia purpurea, Tephrosia hamiltoni, Tephrosia falciformis, Tephrosia vogellii, Tephrosia lanceolata,* etc.

Different parts of the plant are used: the roots are used as a dental product or as a local antiseptic, the leaves are digestives and laxatives and also used as an antiseptic. The barks are used as a vermifuge, and, finally, the seeds are used as a source of karanja oil.

Karanja seeds comprise approximately 27 to 39% of oil.

Karanja oil is obtained from the seeds, by pressing or by extraction with solvent. The press cake, less rich in oil than the seeds, can also be used as raw material. The oils obtained generally have the same physico-chemical properties, being present in the form of a turbid liquid of brown to orange color and with a strong, unpleasant odor.

Karanja oil comprises primarily triglycerides as well as oleic and linoleic acids and, in smaller proportions: palmitic acid, stearic acid, linolenic acid, arachidonic acid as well as behenic acid.

Karanja oil, once extracted from the seeds, is widely used. In the ayurvedic pharmacopoeia, it is used, in particular, for skin care, hair care, in particular for its antiseptic and antiparasitic properties; it is also used in the treatment of eczema, psoriasis, and in the treatment of the scalp. Karanja oil is also used sometimes as an insecticide.

In addition to the above-mentioned traditional uses, Karanja oil has also been used more recently as a sunscreen, alone or in combination with other sunscreens, in cosmetic compositions. In particular, this is due to the presence of certain unsaponifiable compounds. As an indication karanja oil consists of approximately 2 to 5% of unsaponifiables, of which the most known are two diketones: pongamol (CAS 482-33-3) and karanjin (CAS 521-88-0).

Very generally, the average mass percentages of pongamol and karanjin in karanja oils are between 0.3 and 0.9% for pongamol and between 2 and 4% for karanjin.

These mass percentages are given as an indication only, since they can vary widely depending on the species, the season, the site of collection, etc.

The sun protection properties of karanja oil are essentially due to the presence of pongamol, the latter is a natural filter having a UV absorption spectrum similar to that of methoxydibenzoylmethane (CAS 70356-09-1), better known under the tradename of PARSOL 1789®.

However, the incorporation of karanja oil in sunscreen compositions is limited by the organoleptic properties of said oil.

These negative organoleptic properties are essentially due to the presence of karanjin.

The elimination of all or some of the karanjin from the karanja oil thus has the direct effect of increasing the quantity of this oil that can be incorporated in sunscreen cosmetic compositions. Moreover, the maintenance of a sufficient mass percentage of pongamol is important in order to preserve good sunscreen properties.

However, the selective elimination of karanjin is difficult due to the chemical relatedness existing between karanjin and pongamol.

In the application WO 2014/016349 in the name of BIOSYNTHIS, a sunscreen composition is disclosed, which comprises karanja oil as well as other compounds, and, in particular, a polyester. In this application, there is no mention at all of a selective extraction process.

In the publication "Exhibitors Suppliers Day—USA," May 1, 2013 (2013-05-01), pages 1-16, XP055264364 (http://www.youbuyfrance.com/medias/press/2013-03-05-cataloguefrench-pavilion-suppliers-day_7_5_2013_59_19.pdf), mention is made of a BIOSYNTHIS stand, and, in particular, of the product KARANSUN®, this product of 2013 comprising no diester.

The application WO 2014114888 in the name of Jean-Noël THOREL relates to a system for protection against UV radiation and free radicals, which is based on the combination of karanja oil and penthaerythrityl tetra-di-t-butyl hydroxyhydrocinnamate.

The publication "FPS 40 Sun Cream for the Face," GNP D; MINTEL, Sep. 1, 2008 (2008 Sep. 1), XP002716746 relates to a commercial composition comprising karanja oil as well as pongamol. Pongamol is added in addition to the pongamol contained in karanja oil, the concentration of pongamol in karanja oil being apparently insufficient.

The application FR 2720643 in the name of CLARINS relates to a cosmetic preparation intended to improve the condition of the skin; no explicit mention of a sunscreen product is made. Karanja oil is given as an example of an active ingredient capable of having an effect on UV radiation.

In a commercial publication (GIVAUDAN: Leading sensory innovation: *Pongamia* extract and karanja oil, Issue 004 April 2008), the sunscreen effects of compositions comprising pure pongamol are extoled. On page 11, pure pongamol is characterized (minimum content of 90%).

In the patent FR 2762008 in the name of PIERRE FABRE, a process for deodorizing karanja oil is disclosed. Other cosmetic applications of karanja oil are also described therein, in particular, anti-wrinkle and hydrating properties.

In the application GB 2237805 in the name of UNILEVER PLC, a process for extracting diketone is disclosed, this process comprises two steps: extraction with an organic acid and separation of the interfering diketone molecules. More precisely, it is an extraction of pongamol. It is specified that karanja oil, after removal of the pongamol, is used for the production of soaps; the final oil is thus relatively free of pongamol. As far as the pongamol is concerned, crystals form during the process; said pongamol having a melting point between 126° C. and 127.5° C., the pongamol obtained thus appears to be relatively pure.

In the application WO 2014195639 in the name of VALAGRO, a process for extracting unsaponifiables from a renewable lipid raw material is disclosed. Example 1 relates most particularly to the selective extraction of pongamol and of karanjin. The process consists primarily of two steps, a first solid/liquid extraction step carried out with a percolator with circulation and recirculation of an ethanol/hexane mixture through the crushed and previously dried seeds, as well as a step of concentration by evaporation of the solvent.

In summary, no document of the prior art discloses an economic process for selective extraction of karanjin that is environmentally friendly, inexpensive and easy to carry out.

This is probably due to the difficulties that the person skilled in the art encounters in the selective extraction of two structurally similar molecules.

Thus, there is an advantage in having an improved selective extraction process.

Surprisingly, it has been shown that it is possible to selectively extract karanjin by means of a process having all the following positive features: economical, environmentally friendly, inexpensive and easy to carry out by selectively solubilizing pongamol by means of solvents of diester type which are compatible with the requirements of the cosmetic industry.

Among these diesters, one considers, in particular, the compounds having the following formula (I), or mixtures thereof:

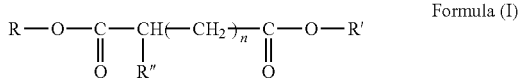

Formula (I)

in which:

n is from 0 to 19;

R and R', which may be identical or different, are alkyls derived from an esterification by a linear or branched alcohol of molecular formula $C_xH_{2x+2}O$, x being from 1 to 30, preferably from 1 to 20, preferably from 1 to 10.

R" is either a hydrogen atom or a $C_1$-$C_3$ alkyl group.

These diesters have flash points above 70° C. and thus they do not entail the risks of VOC of which the flash points are below 70° C.

In the context of the present invention, some diesters are particularly preferable, such as, for example, the sebacates (n=7), the adipates (n=3), the succinates (n=1), the dodecanedioates (n=9), the azelates (n=6), the glutarates (n=2), the malonates (n=0), etc.

The invention relates to a cosmetic ingredient, characterized in that it consists of a solution of at least one extract of karanja oil comprising pongamol (CAS 484-33-3) and karanjin (CAS 521-88-0) in at least one solvent selected from the group of diesters having the following formula (I), or mixtures thereof:

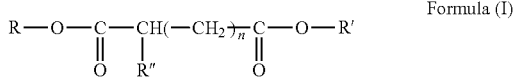

Formula (I)

in which:

n is from 0 to 19;

R and R', which may be identical or different, are selected from the group of the alkyls derived from a linear or branched alcohol of molecular formula $C_xH_{2x+2}O$ before the esterification, x being from 1 to 30, preferably from 1 to 20, preferably from 1 to 10.

R" is either a hydrogen atom or a $C_1$-$C_3$ alkyl group.

The invention also relates to a process of selective precipitation of pongamol (CAS 484-33-3) in karanja oil comprising pongamol (CAS 484-33-3) and karanjin (CAS 521-88-0), characterized in that it comprises:

1) at least one step of addition to said at least one karanja oil of at least one solvent selected from the group of the diesters having the following formula (I), or mixtures thereof:

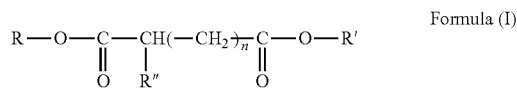

Formula (I)

in which:

n is from 0 to 19;

R and R', which may be identical or different, are alkyls derived from an esterification by a linear or branched alcohol of molecular formula $C_xH_{2x+2}O$, x being from 1 to 30, preferably from 1 to 20, preferably from 1 to 10.

R" is either a hydrogen atom or a $C_1$-$C_3$ alkyl group.

said addition having the effect of forming a light mass phase (supernatant) in the form of a solution and a heavy phase in the form of a precipitate; and 2) at least one step of separation of the two phases obtained.

The invention also relates to a cosmetic formulation, characterized in that it comprises:

a cosmetic ingredient according to the invention;

a cosmetically acceptable vehicle.

The invention also relates to the use of a cosmetic formulation according to the invention as described above, as a solar cosmetic formulation.

The invention also relates to the use of a cosmetic formulation according to the invention as described above, as an anti-aging cosmetic formulation.

In addition to the ecological and economical advantages, the process according to the invention allows the obtention, with a process comprising few steps, of a pongamol-enriched solution which is ready to be formulated directly without requiring a step of melting or hot dissolution of the pongamol before incorporation in a cosmetic formulation, as must be done when pure pongamol is used.

From the economic standpoint and from the standpoint of environmental friendliness and cost, the process which can be carried out at ambient temperature makes it possible to achieve a savings of resources, to the extent that no solvent is eliminated during the process. In addition, no toxic solvent is used, in particular, no flammable solvent classified as a light VOC (flash point <70° C.) is used.

The process also makes it possible to use biosourced solvents such as the sebacates, the succinates and the azelates which have a better environmental impact than their homologs of fossil origin. In addition, the extraction of the unsaponifiable fraction preserves the triglycerides, which can in turn be developed, since the process does not include a step of saponification or hydrolysis.

From the standpoint of facility of implementation, the process comprises a limited number of steps which are relatively simple to carry out. In particular, it presents no step of conditioning the seed (drying, crushing, flattening, etc.) which is required, for example, by the process described in the application WO 2014195639 in the name of VALAGRO.

A brief description of the drawings follows.

Figure 1:
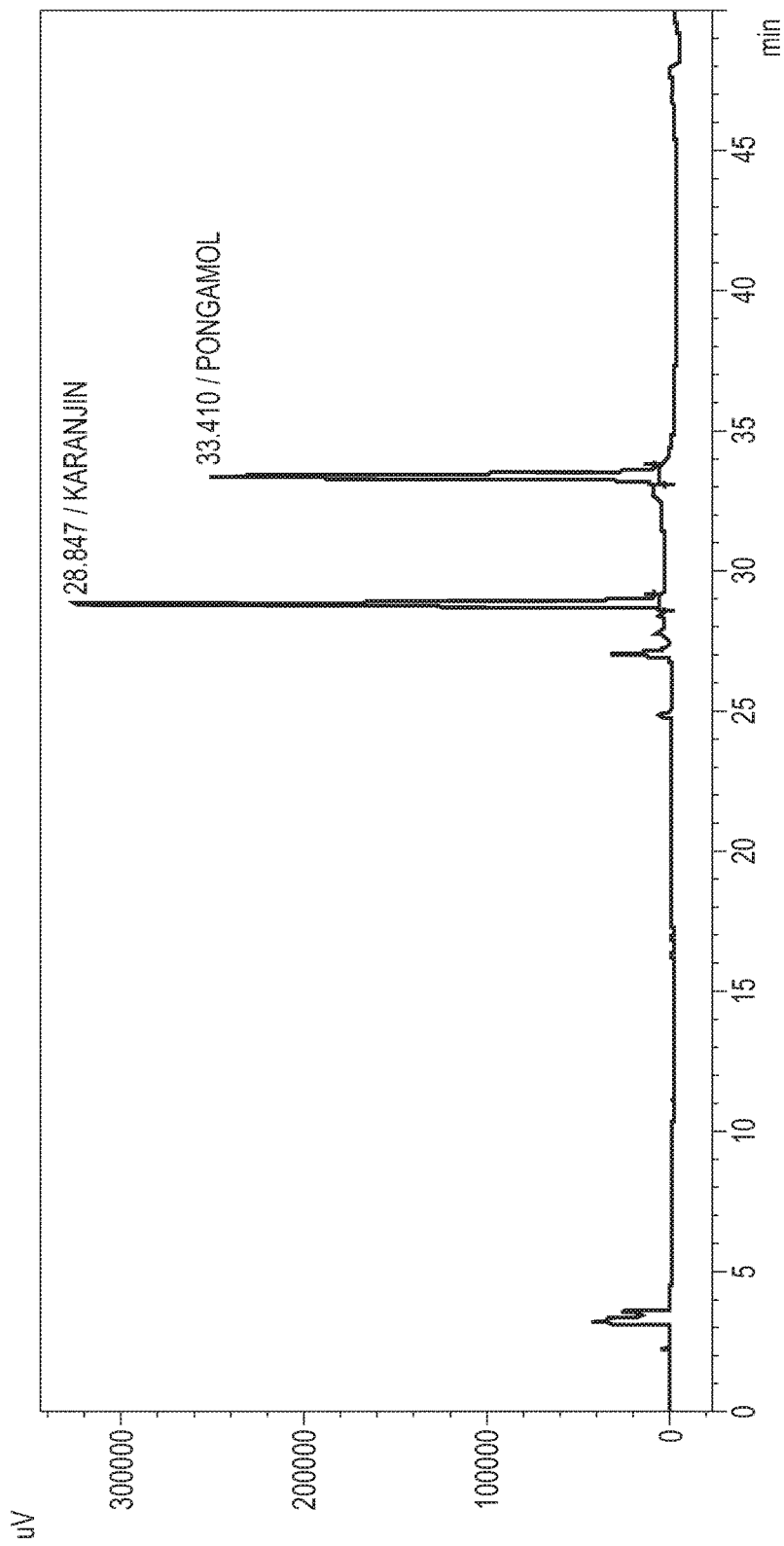
FIG. 1 is a chromatogram of a calibration stock solution of karanjin and pongamol used in Example 1.

A certain number of definitions are given below.

The term "karanja oil" Is used to refer to any oil derived from a plant of the karanja family. This can be, in particular, the following plant species: *Pongamia glabra, Pongamia pinnata, Milletia pinnata, Derris indica, Gadelupa pinnata, Pongamia grandifolia, Robinia mitis, Tephrosia purpurea, Tephrosia hamiltoni, Tephrosia falciformis, Tephrosia vogellii, Tephrosia lanceolata*, etc. The karanja oil can be "raw," that is to say obtained directly from seeds by cold pressing or extraction by means of a solvent with elimination of the solvent.

The karanja oil can also undergo treatments to purify it by eliminating impurities from it in particular, by deodorizing it or by bleaching it.

For example, the treatment can consist of one or more molecular distillations and/or of a mucilage removal and/or of one or more deodorizations.

The term "light phase (supernatant)" is used to refer to the light phase derived from the selective precipitation step. It is a solution. It is separated from the heavy phase (precipitate) by processes well known to the person skilled in the art, which can be, for example, centrifugation or filtration. The light phase (supernatant) is of quite particular interest, to the extent that, once separated from the heavy phase (precipitate), the light phase (supernatant) which is a solution constitutes the cosmetic ingredient according to the invention.

The term "heavy phase (precipitate)" is used to refer to the heavy phase derived from the selective precipitation step. It is separated from the light phase (supernatant) by processes well known to the person skilled in the art, which can be, for example, centrifugation or filtration.

The term "selective precipitation" is used to refer to a precipitation allowing the precipitation, in particular, of a chemical species from a mixture. In the selective precipitation process according to the invention, karanjin is preferably precipitated with respect to the pongamol. For example, if, during a precipitation step, the precipitate consists of 61.5% of karanjin and of only 4.3% of pongamol, a selective precipitation of karanjin occurs.

The term "mass percentage" (expressed in %) is used to refer to the ratio between the mass of a constituent of a mixture and the total mass of the mixture. For example, if a constituent i of a mixture has a mass of 1 kg, and if the mixture has a mass of 100 kg, the mass percentage of the constituent i is 1%. For example, when a cosmetic ingredient according to the invention is characterized in that the mass percentage of pongamol in the solution (of which the cosmetic ingredient is entirely constituted) is 3%, this means that in 100 g of cosmetic ingredient/solution, there are 3 g of pongamol.

The term "extraction yield" is used to refer to the ratio between the mass of a component before a step (for example, a selective precipitation step) and the mass of the same component after said step. In particular, it can be expressed as a percentage, and is from 0% to 100%. For example, the extraction yield of pongamol during the precipitation is calculated as follows: mass of pongamol in the karanja oil before the precipitation/mass of pongamol in the solution obtained at the end of the precipitation. When the term "extraction yield in a phase" is used, it refers to the ratio between the mass of a component in the phase and the mass of the same component before the step that led to the formation of the phase.

The term "multiplication of the $m_{pongamol}/m_{karanjin}$ ratio" is used to refer to the multiplication of the ratio of the $m_{pongamol}/m_{karanjin}$ masses during one or more steps of the process, expressed as follows:

$$\text{Multiplication of the } \frac{mpongamol}{mkaranjin}\text{ratio} = \frac{\frac{mpongamol}{mkaranjin}\text{ratio after the step(s)}}{\frac{mpongamol}{mkaranjin}\text{ratio before the step(s)}}$$

For example, it can pertain to the multiplication of the $m_{pongamol}/m_{karanjin}$ mass ratio during steps 1) and 2), the comparison is then made between the $m_{pongamol}/m_{karanjin}$ mass ratio before step 1) and the $m_{pongamol}/m_{karanjin}$ ratio after step 2); if, before step 1), the $m_{pongamol}/m_{karanjin}$ ratio is 0.71, and after step 2), the $m_{pongamol}/m_{karanjin}$ ratio (in the solution derived from the recovery of the light phase or supernatant) is 1.75, then the multiplication of the $m_{pongamol}/m_{karanjin}$ ratio is calculated as follows: 1.75/0.71=2.46. The $m_{pongamol}/m_{karanjin}$ ratio was multiplied by a factor of 2.46 in steps 1) and 2).

The term "photostability" is used to refer to the stability of any compound, in particular, a cosmetic ingredient according to the invention, with respect to the degradation induced by light radiation or photodegradation.

The invention relates to a cosmetic ingredient, characterized in that it consists of a solution of at least one extract of karanja oil comprising pongamol (CAS 484-33-3) and karanjin (CAS 521-88-0) in at least one solvent selected from the group of the diesters having the following formula (I), or mixtures thereof:

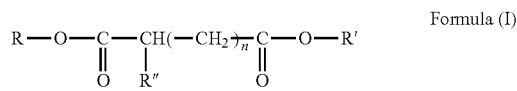

Formula (I)

in which:

n is from 0 to 19;

R and R', which may be identical or different, are alkyls derived from an esterification by a linear or branched alcohol of molecular formula $C_xH_{2x+2}O$, x being from 1 to 30, preferably from 1 to 20, preferably from 1 to 10.

R" is either a hydrogen atom or a $C_1$-$C_3$ alkyl group.

In an embodiment, the cosmetic ingredient according to the invention is characterized in that R" is a hydrogen atom.

In an embodiment, the cosmetic ingredient according to the invention is characterized in that R" is a methyl.

In an embodiment, the cosmetic ingredient according to the invention is characterized in that x is from 1 to 20.

In an embodiment, the cosmetic ingredient according to the invention is characterized in that x is from 1 to 10.

In an embodiment, the cosmetic ingredient according to the invention is characterized in that n is from 1 to 10.

In an embodiment, the cosmetic ingredient according to the invention is characterized in that R is identical to R'.

In an embodiment, the cosmetic ingredient according to the invention is characterized in that R is different from R'.

In an embodiment, the cosmetic ingredient according to the invention is characterized in that said at least one solvent is selected from the group consisting of the sebacates (n=7), the adipates (n=3), the succinates (n=1), the dodecanedioates (n=9), the azelates (n=6), the glutarates (n=2), the malonates (n=0), and mixtures thereof.

In an embodiment, the cosmetic ingredient according to the invention is characterized in that said at least one solvent is selected from the group consisting of the sebacates (n=7).

In an embodiment, the cosmetic ingredient according to the invention is characterized in that said at least one solvent is selected from the group consisting of the adipates (n=3).

In an embodiment, the cosmetic ingredient according to the invention is characterized in that said at least one solvent is selected from the group consisting of the succinates (n=1).

In an embodiment, the cosmetic ingredient according to the invention is characterized in that said at least one solvent is selected from the group consisting of the dodecanedioates (n=9).

In an embodiment, the cosmetic ingredient according to the invention is characterized in that said at least one solvent is selected from the group consisting of the azelates (n=6).

In an embodiment, the cosmetic ingredient according to the invention is characterized in that said at least one solvent is selected from the group consisting of the glutarates (n=2).

In an embodiment, the cosmetic ingredient according to the invention is characterized in that said at least one solvent is selected from the group consisting of the malonates (n=0).

The sebacates are widely used solvents. They are derivatives of sebacic acid or decanedioic acid (CAS 111-20-6) which is a dicarboxylic acid with 10 carbons having the following formula:

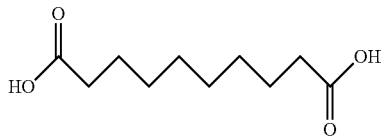 [SMILES: O=C(O)CCCCCCCCC(=O)O]

The sebacic acid can be doubly esterified by the use of two identical or different alcohols.

In an embodiment, the cosmetic ingredient according to the invention is characterized in that said at least one solvent is a sebacic acid doubly esterified by two identical or different alcohols, each of the two alcohols being a linear or branched alcohol, or a mixture of isomers in any proportions where appropriate, or a single one of the isomers where appropriate, the alcohol being a $C_1$-$C_{30}$ alcohol, preferably a $C_1$-$C_{20}$ alcohol, preferably a $C_1$-$C_{10}$ alcohol.

In an embodiment, the cosmetic ingredient according to the invention is characterized in that said at least one solvent is a sebacic acid doubly esterified by two identical or different alcohols, each of the two alcohols being selected from the group consisting of methanol, ethanol, the propanols of molecular formula $C_3H_8O$, the butanols of molecular formula $C_4H_{10}O$, the pentanols of molecular formula $C_5H_{12}O$, the hexanols of molecular formula $C_6H_{14}O$, the heptanols of molecular formula $C_7H_{16}O$, the octanols of molecular formula $C_8H_{18}O$, the nonanols of molecular formula $C_9H_{20}O$, the decanols of molecular formula $C_{10}H_{22}O$, the undecanols of molecular formula $C_{11}H_{24}O$, the dodecanols of molecular formula $C_{12}H_{26}O$, the tridecanols of molecular formula $C_{13}H_{28}O$, the tetradecanols of molecular formula $C_{14}H_{30}O$, the pentadecanols of molecular formula $C_{15}H_{32}O$, the hexadecanols of molecular formula $C_{16}H_{34}O$, the heptadecanols of empirical $C_{17}H_{36}O$, the octadecanols of molecular formula $C_{18}H_{38}O$, the nonadecanols of molecular formula $C_{19}H_{40}O$ and the eicosanols of molecular formula $C_{20}H_{42}O$.

In an embodiment, the cosmetic ingredient according to the invention is characterized in that said at least one solvent is a sebacic acid doubly esterified by two identical or different alcohols, each of the two alcohols being selected from the group consisting of methanol (CAS 67-56-1), ethanol (CAS 64-17-5), propan-1-ol (or n-propanol) (CAS 71-23-8), propan-2-ol (or isopropanol) (CAS 67-63-0), butan-1-ol (or n-butanol) (CAS 71-36-3), (R)-butan-2-ol (CAS 14898-79-4), (S)-butan-2-ol (CAS 4221-99-2), 2-methylpropan-1-ol (CAS 78-83-1), 2-methylpropan-2-ol (CAS 75-65-0), 2-methylpropan-2-ol (CAS 75-65-0), pentan-1-ol (CAS 71-41-0), 3-methylbutan-1-ol (CAS 123-51-3), 2-methylbutan-1-ol (CAS 137-32-6), 2,2-dimethylpropan-1-ol (CAS 75-84-3), pentan-3-ol (CAS 584-02-1), pentan-2-ol (CAS 6032-29-7), 3-methylbutan-2-ol (CAS 598-75-4), 2-methylbutan-2-ol (CAS 75-85-4), hexan-1-ol (CAS 111-27-3), heptan-1-ol (CAS 111-70-6), dodecan-1-ol (CAS 112-53-8), octan-1-ol (CAS 111-87-5), 2-ethylhexan-1-ol (CAS 104-76-7), octadecan-1-ol (CAS 112-92-5), decan-1-ol (CAS 112-30-1) and dodecan-1-ol (CAS 112-53-8).

In an embodiment, the cosmetic ingredient according to the invention is characterized in that said at least one solvent is selected from the group consisting of dioctyl sebacate (CAS 122-62-3), diethyl sebacate (CAS 110-40-7), dibutyl sebacate (CAS 109-43-3), diisopropyl sebacate (CAS 7491-02-3), and mixtures thereof.

In an embodiment, the cosmetic ingredient according to the invention is characterized in that said at least one solvent is selected from the group consisting of diethyl sebacate (CAS 110-40-7), dibutyl sebacate (CAS 109-43-3), diisopropyl sebacate (CAS 7491-02-3), and mixtures thereof.

In an embodiment, the cosmetic ingredient according to the invention is characterized in that said at least one solvent is diethyl sebacate (CAS 110-40-7).

Sebacic acid diesters are used in cosmetology. In the application WO 9850005 in the name of MEDLOGIC GLOBAL CORPORATION, diethyl sebacate is mentioned as solvent, and diisopropyl sebacate and dibutyl sebacate are mentioned as emollients.

In the U.S. Pat. No. 5,152,983 In the name of CHESEBROUGH-POND'S USA CO, dibutyl sebacate is mentioned as emollient, and the addition of pongamol to the composition is provided for. In the composition of example 1, a sunscreen composition comprising pongamol is tested.

Adipates are widely used solvents. They are derivatives of adipic acid (CAS 124-04-9) which is an aliphatic dicarboxylic acid having the following formula:

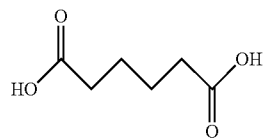

Adipic acid can be doubly esterified by the use of two identical or different alcohols.

In an embodiment, the cosmetic ingredient according to the invention is characterized in that said at least one solvent is a sebacic acid doubly esterified by two identical or different alcohols, each of the two alcohols being a linear or branched alcohol, or a mixture of isomers in any proportions where appropriate, or a single one of the isomers where appropriate, the alcohol being a $C_1$-$C_{30}$ alcohol, preferably a $C_1$-$C_{20}$ alcohol, preferably a $C_1$-$C_{10}$ alcohol.

In an embodiment, the cosmetic ingredient according to the invention is characterized in that at least one solvent is an adipic acid doubly esterified by two identical or different alcohol, each of the two alcohols being selected from the group consisting of methanol, ethanol, the propanols of molecular formula $C_3H_8O$, the butanols of molecular formula $C_4H_{10}O$, the pentanols of molecular formula $C_5H_{12}O$, the hexanols of molecular formula $C_6H_{14}O$, the heptanols of molecular formula $C_7H_{16}O$, the octanols of molecular formula $C_8H_{18}O$, the nonanols of molecular formula $C_9H_{20}O$, the decanols of molecular formula $C_{10}H_{22}O$, the undecanols of molecular formula $C_{11}H_{24}O$, the dodecanols of molecular formula $C_{12}H_{26}O$, the tridecanols of molecular formula $C_{13}H_{28}O$, the tetradecanols of molecular formula $C_{14}H_{30}O$, the pentadecanols of molecular formula $C_{15}H_{32}O$, the hexadecanols of molecular formula $C_{16}H_{34}O$, the heptadecanols of molecular formula $C_{17}H_{36}O$, the octadecanols of molecular formula $C_{18}H_{38}O$, the nonadecanols of molecular formula $C_{19}H_{40}O$ and the eicosanols of molecular formula $C_{20}H_{42}O$.

In an embodiment, the cosmetic ingredient according to the invention is characterized in that said at least one solvent is an adipic acid doubly esterified by two identical or different alcohols, each of the two alcohols being selected from the group consisting of methanol (CAS 67-56-1), ethanol (CAS 64-17-5), propan-1-ol (or n-propanol) (CAS 71-23-8), propan-2-ol (or isopropanol) (CAS 67-63-0), butan-1-ol (or n-butanol) (CAS 71-36-3), (R)-butan-2-ol (CAS 14898-79-4), (S)-butan-2-ol (CAS 4221-99-2), 2-methylpropan-1-ol (CAS 78-83-1), 2-methylpropan-2-ol (CAS 75-65-0), 2-methylpropan-2-ol (CAS 75-65-0), pentan-1-ol (CAS 71-41-0), 3-methylbutan-1-ol (CAS 123-51-3), 2-methylbutan-1-ol (CAS 137-32-6), 2,2-dimethylpropan-1-ol (CAS 75-84-3), pentan-3-ol (CAS 584-02-1), pentan-2-ol (CAS 6032-29-7), 3-methylbutan-2-ol (CAS 598-75-4), 2-methylbutan-2-ol (CAS 75-85-4), hexan-1-ol (CAS 111-27-3), heptan-1-ol (CAS 111-70-6), dodecan-1-ol (CAS 112-53-8), octan-1-ol (CAS 111-87-5), 2-ethylhexan-1-ol (CAS 104-76-7), octadecan-1-ol (CAS 112-92-5), decan-1-ol (CAS 112-30-1) and dodecan-1-ol (CAS 112-53-8).

In an embodiment, the cosmetic ingredient according to the invention is characterized in that said at least one solvent is selected from the group consisting of dihexyl adipate (CAS 2091-24-9), diisostearyl adipate (CAS 62479-36-1), dicapryl adipate (CAS 108-63-4), di-C12-15 alkyl adipate, ditridecyl adipate (CAS 16958-92-2), dicetyl adipate (CAS 26720-21-8), diisopropyl adipate (CAS 6938-94-9), diisobutyl adipate (CAS 141-04-8), diethylhexyl adipate (CAS 103-23-1), diisooctyl adipate (CAS 1330-86-5), diisononyl adipate (CAS 33703-08-1), diisodecyl adipate (CAS 27178-16-1), diethyl adipate (CAS 141-28-6), dimethyl adipate (CAS 627-93-0), dihexyldecyl adipate (CAS 57533-90-1), diheptylundecyl adipate (CAS 155613-91-5), dipropyl adipate (CAS 106-19-4), dioctyldodecyl adipate (CAS 85117-94-8), dibutyl adipate (CAS 105-99-7), diisocetyl adipate (CAS 57533-90-1), dioctyl adipate (CAS 123-79-5), and mixtures thereof.

In an embodiment, the cosmetic ingredient according to the invention is characterized in that said at least one solvent is selected from the group consisting of diisopropyl adipate (CAS 6938-94-9), dibutyl adipate (CAS 105-99-7), dioctyl adipate (CAS 123-79-5), and mixtures thereof.

Succinates are widely used solvents. They are derivatives of succinic acid (CAS 110-15-6) having the following formula:

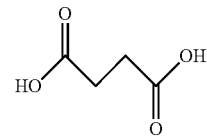

Succinic acid can be doubly esterified by the use of two identical or different alcohols.

In an embodiment, the cosmetic ingredient according to the invention is characterized in that at least one solvent is sebacic acid doubly esterified by two identical or different alcohols, each of the two alcohols being a linear or branched alcohol, or a mixture of isomers in any proportions where appropriate, or a single one of the isomers where appropriate, the alcohol being a $C_1$-$C_{30}$ alcohol, preferably a $C_1$-$C_{20}$ alcohol, preferably a $C_1$-$C_{10}$ alcohol.

In an embodiment, the cosmetic ingredient according to the invention is characterized in that said at least one solvent is a succinic acid doubly esterified by two identical or different alcohols, each of the two alcohols being selected from the group consisting of methanol, ethanol, the propanols of molecular formula $C_3H_8O$, the butanols of molecular formula $C_4H_{10}O$, the pentanols of molecular formula $C_5H_{12}O$, the hexanols of molecular formula $C_6H_{14}O$, the heptanols of molecular formula $C_7H_{16}O$, the octanols of molecular formula $C_8H_{18}O$, the nonanols of molecular formula $C_9H_{20}O$, the decanols of molecular formula $C_{10}H_{22}O$, the undecanols of molecular formula $C_{11}H_{24}O$, the dodecanols of molecular formula $C_{12}H_{26}O$, the tridecanols of molecular formula $C_{13}H_{28}O$, the tetradecanols of molecular formula $C_{14}H_{30}O$, the pentadecanols of molecular formula $C_{15}H_{32}O$, the hexadecanols of molecular formula $C_{16}H_{34}O$, the heptadecanols of molecular formula $C_{17}H_{36}O$, the octadecanols of molecular formula $C_{18}H_{38}O$, the nonadecanols of molecular formula $C_{19}H_{40}O$ and the eicosanols of molecular formula $C_{20}H_{42}O$.

In an embodiment, the cosmetic ingredient according to the invention is characterized in that said at least one solvent is a succinic acid doubly esterified by two identical or different alcohols, each of the two alcohols being selected from the group consisting of methanol (CAS 67-56-1), ethanol (CAS 64-17-5), propan-1-ol (or n-propanol) (CAS 71-23-8), propan-2-ol (or isopropanol) (CAS 67-63-0), butan-1-ol (or n-butanol) (CAS 71-36-3), (R)-butan-2-ol (CAS 14898-79-4), (S)-butan-2-ol (CAS 4221-99-2), 2-methylpropan-1-ol (CAS 78-83-1), 2-methylpropan-2-ol (CAS 75-65-0), 2-methylpropan-2-ol (CAS 75-65-0), pentan-1-ol (CAS 71-41-0), 3-methylbutan-1-ol (CAS 123-51-3), 2-methylbutan-1-ol (CAS 137-32-6), 2,2-dimethylpropan-1-ol (CAS 75-84-3), pentan-3-ol (CAS 584-02-1), pentan-2-ol (CAS 6032-29-7), 3-methylbutan-2-ol (CAS 598-75-4), 2-methylbutan-2-ol (CAS 75-85-4), hexan-1-ol (CAS 111-27-3), heptan-1-ol (CAS 111-70-6), dodecan-1-ol (CAS 112-53-8), octan-1-ol (CAS 111-87-5), 2-ethylhexan-1-ol (CAS 104-76-7), octadecan-1-ol (CAS 112-92-5), decan-1-ol (CAS 112-30-1) and dodecan-1-ol (CAS 112-53-8).

In an embodiment, the cosmetic ingredient according to the invention is characterized in that said at least one solvent is selected from the group consisting of didecyl succinate (CAS 10595-82-1), dimethyl succinate (CAS 106-65-0), diethyl succinate (CAS 123-25-1), dicapryl succinate (CAS 14491-66-8), dicetearyl succinate (CAS 93280-98-9), diisobutyl succinate (CAS 925-06-4), diethylhexyl succinate (CAS 2915-57-3), and mixtures thereof.

In an embodiment, the cosmetic ingredient according to the invention is characterized in that said at least one solvent is diethylhexyl succinate (CAS 2915-57-3).

2-Methylsuccinates are derivatives of 2-methylsuccinic acid (CAS 498-21-5) having the following formula:

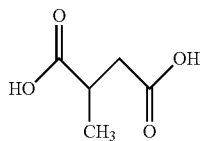

2-Methylsuccinic acid can be doubly esterified by the use of two identical or different alcohols.

In an embodiment, the cosmetic ingredient according to the invention is characterized in that said at least one solvent is a 2-methylsuccinic acid doubly esterified by two identical or different alcohols, each of the two alcohols being a linear or branched alcohol, or a mixture of isomers in any proportions where appropriate, or a single one of the isomers where appropriate, the alcohol being a $C_1$-$C_{30}$ alcohol, preferably a $C_1$-$C_{20}$ alcohol, preferably a $C_1$-$C_{10}$ alcohol.

In an embodiment, the cosmetic ingredient according to the invention is characterized in that said at least one solvent is a 2-methylsuccinic acid doubly esterified by two identical or different alcohols, each of the two alcohols being selected from the group consisting of methanol, ethanol, the propanols of molecular formula $C_3H_8O$, the butanols of molecular formula $C_4H_{10}O$, the pentanols of molecular formula $C_5H_{12}O$, the hexanols of molecular formula $C_6H_{14}O$, the heptanols of molecular formula $C_7H_{16}O$, the octanols of molecular formula $C_8H_{18}O$, the nonanols of molecular formula $C_9H_{20}O$, the decanols of molecular formula $C_{10}H_{22}O$, the undecanols of molecular formula $C_{11}H_{24}O$, the dodecanols of molecular formula $C_{12}H_{26}O$, the tridecanols of molecular formula $C_{13}H_{28}O$, the tetradecanols of molecular formula $C_{14}H_{30}O$, the pentadecanols of molecular formula $C_{15}H_{32}O$, the hexadecanols of molecular formula $C_{16}H_{34}O$, the heptadecanols of molecular formula $C_{17}H_{36}O$, the octadecanols of molecular formula $C_{18}H_{38}O$, the nonadecanols of molecular formula $C_{19}H_{40}O$ and the eicosanols of molecular formula $C_{20}H_{42}O$.

In an embodiment, the cosmetic ingredient according to the invention is characterized in that said at least one solvent is a 2-methylsuccinic acid doubly esterified by two identical or different alcohols, each of the two alcohols being selected from the group consisting of methanol (CAS 67-56-1), ethanol (CAS 64-17-5), propan-1-ol (or n-propanol) (CAS 71-23-8), propan-2-ol (or isopropanol) (CAS 67-63-0), butan-1-ol (or n-butanol) (CAS 71-36-3), (R)-butan-2-ol (CAS 14898-79-4), (S)-butan-2-ol (CAS 4221-99-2), 2-methylpropan-1-ol (CAS 78-83-1), 2-methylpropan-2-ol (CAS 75-65-0), 2-methylpropan-2-ol (CAS 75-65-0), pentan-1-ol (CAS 71-41-0), 3-methylbutan-1-ol (CAS 123-51-3), 2-methylbutan-1-ol (CAS 137-32-6), 2,2-dimethylpropan-1-ol (CAS 75-84-3), pentan-3-ol (CAS 584-02-1), pentan-2-ol (CAS 6032-29-7), 3-methylbutan-2-ol (CAS 598-75-4), 2-methylbutan-2-ol (CAS 75-85-4), hexan-1-ol (CAS 111-27-3), heptan-1-ol (CAS 111-70-6), dodecan-1-ol (CAS 112-53-8), octan-1-ol (CAS 111-87-5), 2-ethylhexan-1-ol (CAS 104-76-7), octadecan-1-ol (CAS 112-92-5), decan-1-ol (CAS 112-30-1) and dodecan-1-ol (CAS 112-53-8).

In an embodiment, the cosmetic ingredient according to the invention is characterized in that said at least one solvent is selected from the group consisting of diethyl 2-methylsuccinate (CAS 4676-51-1), 1-ethyl and 4-methyl 2-methylsuccinate (CAS 204125-41-7), 1-methyl and 4-methyl 2-methylsuccinate (CAS 606491-29-6), dipropyl 2-methylsuccinate (CAS 56108-32-8), diisopropyl 2-methylsuccinate (CAS 75906-62-6), 1-butyl and 4-methyl 2-methylsuccinate (CAS 878209-18-8), di(2-methylpropyl) 2-methylsuccinate (CAS 18447-89-7), 1-pentyl and 4-methyl 2-methylsuccinate (CAS 204125-40-6), 1-methyl and 4-hexyl 2-methylsuccinate (CAS 214280-22-5), di(1-methylpropyl) 2-methylsuccinate (CAS 57983-31-0), di(1,1-dimethylethyl) 2-methylsuccinate (CAS 108763-17-3), dipentyl 2-methylsuccinate (CAS 56108-33-9), dihexyl 2-methylsuccinate (CAS 32774-96-2), diheptyl 2-methylsuccinate (CAS 51191-78-7), 1-methyl and 4-dodecyl 2-methylsuccinate (CAS 214280-27-0), dioctyl 2-methylsuccinate (CAS 131787-12-7), 1-methyl and 4-octadecyl 2-methylsuccinate, didecyl 2-methylsuccinate, didodecyl or lauryl 2-methylsuccinate, decanyl 2-methylsuccinate, 2-ethylhexanyl 2-methylsuccinate, the isomers and the isomer mixtures thereof, and mixtures thereof.

Dodecanedioates are widely used solvents. They are derivatives of dodecanedioic acid (CAS 693-23-2) which is an aliphatic dicarboxylic acid having the following formula:

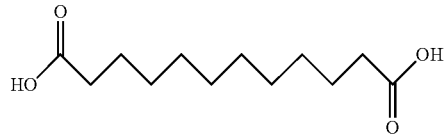 [SMILES: O=C(O)CCCCCCCCCCC(=O)O]

Dodecanedioic acid can be doubly esterified by the use of two identical or different alcohols.

In an embodiment, the cosmetic ingredient according to the invention is characterized in that said at least one solvent is a sebacic acid doubly esterified by two identical or different alcohols, each of the two alcohols being a linear or branched alcohol, or a mixture of isomers in any proportions where appropriate, or a single one of the isomers where appropriate, the alcohol being a $C_1$-$C_{30}$ alcohol, preferably a $C_1$-$C_{20}$ alcohol, preferably a $C_1$-$C_{10}$ alcohol.

In an embodiment, the cosmetic ingredient according to the invention is characterized in that said at least one solvent is a dodecanedioic acid doubly esterified by two identical or different alcohols, each of the two alcohols being selected from the group consisting of methanol, ethanol, the propanols of molecular formula $C_3H_8O$, the butanols of molecular formula $C_4H_{10}O$, the pentanols of molecular formula $C_5H_{12}O$, the hexanols of molecular formula $C_6H_{14}O$, the heptanols of molecular formula $C_7H_{16}O$, the octanols of molecular formula $C_8H_{18}O$, the nonanols of molecular formula $C_9H_{20}O$, the decanols of molecular formula $C_{10}H_{22}O$, the undecanols of molecular formula $C_{11}H_{24}O$, the dodecanols of molecular formula $C_{12}H_{26}O$, the tridecanols of molecular formula $C_{13}H_{28}O$, the tetradecanols of molecular formula $C_{14}H_{30}O$, the pentadecanols of molecular formula $C_{15}H_{32}O$, the hexadecanols of molecular formula $C_{16}H_{34}O$, the heptadecanols of molecular formula $C_{17}H_{36}O$, the octadecanols of molecular formula $C_{18}H_{38}O$, the nonadecanols of molecular formula $C_{19}H_{40}O$ and the eicosanols of molecular formula $C_{20}H_{42}O$.

In an embodiment, the cosmetic ingredient according to the invention is characterized in that said at least one solvent is a dodecanedioic acid doubly esterified by two identical or different alcohols, each of the two alcohols being selected from the group consisting of methanol (CAS 67-56-1), ethanol (CAS 64-17-5), propan-1-ol (or n-propanol) (CAS 71-23-8), propan-2-ol (or isopropanol) (CAS 67-63-0), butan-1-ol (or n-butanol) (CAS 71-36-3), (R)-butan-2-ol (CAS 14898-79-4), (S)-butan-2-ol (CAS 4221-99-2), 2-methylpropan-1-ol (CAS 78-83-1), 2-methylpropan-2-ol (CAS 75-65-0), 2-methylpropan-2-ol (CAS 75-65-0), pentan-1-ol (CAS 71-41-0), 3-methylbutan-1-ol (CAS 123-51-3), 2-methylbutan-1-ol (CAS 137-32-6), 2,2-dimethylpropan-1-ol (CAS 75-84-3), pentan-3-ol (CAS 584-02-1), pentan-2-ol (CAS 6032-29-7), 3-methylbutan-2-ol (CAS 598-75-4), 2-methylbutan-2-ol (CAS 75-85-4), hexan-1-ol (CAS 111-27-3), heptan-1-ol (CAS 111-70-6), dodecan-1-ol (CAS 112-53-8), octan-1-ol (CAS 111-87-5), 2-ethylhexan-1-ol (CAS 104-76-7), octadecan-1-ol (CAS 112-92-5), decan-1-ol (CAS 112-30-1) and dodecan-1-ol (CAS 112-53-8).

In an embodiment, the cosmetic ingredient according to the invention is characterized in that said at least one solvent is selected from the group consisting of dioctyldodecyl dodecanedioate (CAS 129423-55-8), diisocetyl dodecanedioate (CAS 131252-83-0), and mixtures thereof.

Azelates are widely used solvents. They are derivatives of azelaic acid (CAS 123-99-9) having the following formula:

Azelaic acid can be doubly esterified by the use of two identical or different alcohols.

In an embodiment, the cosmetic ingredient according to the invention is characterized in that said at least one solvent is a sebacic acid doubly esterified by two identical or different alcohols, each of the two alcohols being a linear or branched alcohol, or a mixture of isomers in any proportions where appropriate, or a single one of the isomers where appropriate, the alcohol being a $C_1$-$C_{30}$ alcohol, preferably a $C_1$-$C_{20}$ alcohol, preferably a $C_1$-$C_{10}$ alcohol.

In an embodiment, the cosmetic ingredient according to the invention is characterized in that said at least one solvent is an azelaic acid doubly esterified by two identical or different alcohols, each of the two alcohols being selected from the group consisting of methanol, ethanol, the propanols of molecular formula $C_3H_8O$, the butanols of molecular formula $C_4H_{10}O$, the pentanols of molecular formula $C_5H_{12}O$, the hexanols of molecular formula $C_6H_{14}O$, the heptanols of molecular formula $C_7H_{16}O$, the octanols of molecular formula $C_8H_{18}O$, the nonanols of molecular formula $C_9H_{20}O$, the decanols of molecular formula $C_{10}H_{22}O$, the undecanols of molecular formula $C_{11}H_{24}O$, the dodecanols of molecular formula $C_{12}H_{26}O$, the tridecanols of molecular formula $C_{13}H_{28}O$, the tetradecanols of molecular formula $C_{14}H_{30}O$, the pentadecanols of molecular formula $C_{15}H_{32}O$, the hexadecanols of molecular formula $C_{16}H_{34}O$, the heptadecanols of empirical $C_{17}H_{36}O$, the octadecanols of molecular formula $C_{18}H_{38}O$, the nonadecanols of molecular formula $C_{19}H_{40}O$ and the eicosanols of molecular formula $C_{20}H_{42}O$.

In an embodiment, the cosmetic ingredient according to the invention is characterized in that said at least one solvent is an azelaic acid doubly esterified by two identical or different alcohols, each of the two alcohols being selected from the group consisting of methanol (CAS 67-56-1), ethanol (CAS 64-17-5), propan-1-ol (or n-propanol) (CAS 71-23-8), propan-2-ol (or isopropanol) (CAS 67-63-0), butan-1-ol (or n-butanol) (CAS 71-36-3), (R)-butan-2-ol (CAS 14898-79-4), (S)-butan-2-ol (CAS 4221-99-2), 2-methylpropan-1-ol (CAS 78-83-1), 2-methylpropan-2-ol (CAS 75-65-0), 2-methylpropan-2-ol (CAS 75-65-0), pentan-1-ol (CAS 71-41-0), 3-methylbutan-1-ol (CAS 123-51-3), 2-methylbutan-1-ol (CAS 137-32-6), 2,2-dimethylpropan-1-ol (CAS 75-84-3), pentan-3-ol (CAS 584-02-1), pentan-2-ol (CAS 6032-29-7), 3-methylbutan-2-ol (CAS 598-75-4), 2-methylbutan-2-ol (CAS 75-85-4), hexan-1-ol (CAS 111-27-3), heptan-1-ol (CAS 111-70-6), dodecan-1-ol (CAS 112-53-8), octan-1-ol (CAS 111-87-5), 2-ethylhexan-1-ol (CAS 104-76-7), octadecan-1-ol (CAS 112-92-5), decan-1-ol (CAS 112-30-1) and dodecan-1-ol (CAS 112-53-8).

In an embodiment, the cosmetic ingredient according to the invention is characterized in that said at least one solvent is selected from the group consisting of dimethyl azelate (CAS 1732-10-1), di(2-ethylhexyl) azelate, and mixtures thereof.

Glutarates are widely used solvents. They are derivatives of glutaric acid (CAS 110-94-1) having the following formula:

Glutaric acid can be doubly esterified by the use of two identical or different alcohols.

In an embodiment, the cosmetic ingredient according to the invention is characterized in that said at least one solvent is a sebacic acid doubly esterified by two identical or different alcohols, each of the two alcohols being a linear or branched alcohol, or a mixture of isomers in any proportions where appropriate, or a single one of the isomers where appropriate, the alcohol being a $C_1$-$C_{30}$ alcohol, preferably a $C_1$-$C_{20}$ alcohol, preferably a $C_1$-$C_{10}$ alcohol.

In an embodiment, the cosmetic ingredient according to the invention is characterized in that said at least one solvent is a glutaric acid doubly esterified by two identical or different alcohols, each of the two alcohols being selected from the group consisting of methanol, ethanol, the propanols of molecular formula $C_3H_8O$, the butanols of molecular formula $C_4H_{10}O$, the pentanols of molecular formula $C_5H_{12}O$, the hexanols of molecular formula $C_6H_{14}O$, the heptanols of molecular formula $C_7H_{16}O$, the octanols of molecular formula $C_8H_{18}O$, the nonanols of molecular formula $C_9H_{20}O$, the decanols of molecular formula $C_{10}H_{22}O$, the undecanols of molecular formula $C_{11}H_{24}O$, the dodecanols of molecular formula $C_{12}H_{26}O$, the tridecanols of molecular formula $C_{13}H_{28}O$, the tetradecanols of molecular formula $C_{14}H_{30}O$, the pentadecanols of molecular formula $C_{15}H_{32}O$, the hexadecanols of molecular formula $C_{16}H_{34}O$, the heptadecanols of molecular formula $C_{17}H_{36}O$, the octadecanols of molecular formula $C_{18}H_{38}O$, the nonadecanols of molecular formula $C_{19}H_{40}O$ and the eicosanols of molecular formula $C_{20}H_{42}O$.

In an embodiment, the cosmetic ingredient according to the invention is characterized in that said at least one solvent is a glutaric acid doubly esterified by two identical or different alcohols, each of the two alcohols being selected from the group consisting of methanol (CAS 67-56-1), ethanol (CAS 64-17-5), propan-1-ol (or n-propanol) (CAS 71-23-8), propan-2-ol (or isopropanol) (CAS 67-63-0), butan-1-ol (or n-butanol) (CAS 71-36-3), (R)-butan-2-ol (CAS 14898-79-4), (S)-butan-2-ol (CAS 4221-99-2), 2-methylpropan-1-ol (CAS 78-83-1), 2-methylpropan-2-ol (CAS 75-65-0), 2-methylpropan-2-ol (CAS 75-65-0), pentan-1-ol (CAS 71-41-0), 3-methylbutan-1-ol (CAS 123-51-3), 2-methylbutan-1-ol (CAS 137-32-6), 2,2-dimethylpropan-1-ol (CAS 75-84-3), pentan-3-ol (CAS 584-02-1), pentan-2-ol (CAS 6032-29-7), 3-methylbutan-2-ol (CAS 598-75-4), 2-methylbutan-2-ol (CAS 75-85-4), hexan-1-ol (CAS 111-27-3), heptan-1-ol (CAS 111-70-6), dodecan-1-ol (CAS 112-53-8), octan-1-ol (CAS 111-87-5), 2-ethylhexan-1-ol (CAS 104-76-7), octadecan-1-ol (CAS 112-92-5), decan-1-ol (CAS 112-30-1) and dodecan-1-ol (CAS 112-53-8).

In an embodiment, the cosmetic ingredient according to the invention is characterized in that said at least one solvent is selected from the group consisting of dimethyl glutarate (CAS 1119-40-0), diisobutyl glutarate (CAS 71195-64-7), diisostearyl glutarate, dimethyl 2-methylglutarate (CAS 14035-94-0), and mixtures thereof.

Malonates are widely used solvents. They are derivatives of malonic acid (CAS 141-82-2) having the following formula:

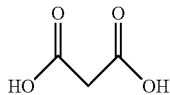

Malonic acid can be doubly esterified by the use of two identical or different alcohols.

In an embodiment, the cosmetic ingredient according to the invention is characterized in that said at least one solvent is a sebacic acid doubly esterified by two identical or different alcohols, each of the two alcohols being a linear or branched alcohol, or a mixture of isomers in any proportions where appropriate, or a single one of the isomers where appropriate, the alcohol being a $C_1$-$C_{30}$ alcohol, preferably a $C_1$-$C_{20}$ alcohol, preferably a $C_1$-$C_{10}$ alcohol.

In an embodiment, the cosmetic ingredient according to the invention is characterized in that said at least one solvent is a malonic acid doubly esterified by two identical or different alcohols, each of the two alcohols being selected from the group consisting of methanol, ethanol, the propanols of molecular formula $C_3H_8O$, the butanols of molecular formula $C_4H_{10}O$, the pentanols of molecular formula $C_5H_{12}O$, the hexanols of molecular formula $C_6H_{14}O$, the heptanols of molecular formula $C_7H_{16}O$, the octanols of molecular formula $C_8H_{18}O$, the nonanols of molecular formula $C_9H_{20}O$, the decanols of molecular formula $C_{10}H_{22}O$, the undecanols of molecular formula $C_{11}H_{24}O$, the dodecanols of molecular formula $C_{12}H_{26}O$, the tridecanols of molecular formula $C_{13}H_{28}O$, the tetradecanols of molecular formula $C_{14}H_{30}O$, the pentadecanols of molecular formula $C_{15}H_{32}O$, the hexadecanols of molecular formula $C_{16}H_{34}O$, the heptadecanols of molecular formula $C_{17}H_{36}O$, the octadecanols of molecular formula $C_{18}H_{38}O$, the nonadecanols of molecular formula $C_{19}H_{40}O$ and the eicosanols of molecular formula $C_{20}H_{42}O$.

In an embodiment, the cosmetic ingredient according to the invention is characterized in that said at least one solvent is a malonic acid doubly esterified by two identical or different alcohols, each of the two alcohols being selected from the group consisting of methanol (CAS 67-56-1), ethanol (CAS 64-17-5), propan-1-ol (or n-propanol) (CAS 71-23-8), propan-2-ol (or isopropanol) (CAS 67-63-0), butan-1-ol (or n-butanol) (CAS 71-36-3), (R)-butan-2-ol (CAS 14898-79-4), (S)-butan-2-ol (CAS 4221-99-2), 2-methylpropan-1-ol (CAS 78-83-1), 2-methylpropan-2-ol (CAS 75-65-0), 2-methylpropan-2-ol (CAS 75-65-0), pentan-1-ol (CAS 71-41-0), 3-methylbutan-1-ol (CAS 123-51-3), 2-methylbutan-1-ol (CAS 137-32-6), 2,2-dimethylpropan-1-ol (CAS 75-84-3), pentan-3-ol (CAS 584-02-1), pentan-2-ol (CAS 6032-29-7), 3-methylbutan-2-ol (CAS 598-75-4), 2-methylbutan-2-ol (CAS 75-85-4), hexan-1-ol (CAS 111-27-3), heptan-1-ol (CAS 111-70-6), dodecan-1-ol (CAS 112-53-8), octan-1-ol (CAS 111-87-5), 2-ethylhexan-1-ol (CAS 104-76-7), octadecan-1-ol (CAS 112-92-5), decan-1-ol (CAS 112-30-1) and dodecan-1-ol (CAS 112-53-8).

In an embodiment, the cosmetic ingredient according to the invention is characterized in that said at least one solvent is diethyl malonate (CAS 105-53-3).

In an embodiment, the cosmetic ingredient according to the invention is characterized in that said extract of karanja oil is extracted from a species selected from the group consisting of *Pongamia glabra, Pongamia pinnata, Milletia pinnata, Derris indica, Gadelupa pinnata, Pongamia grandifolia, Robinia mitis, Tephrosia purpurea, Tephrosia hamiltoni, Tephrosia falciformis, Tephrosia vogellii* and *Tephrosia lanceolata*.

In an embodiment, the cosmetic ingredient according to the invention is characterized in that said extract of karanja oil is extracted from a species selected from the group consisting of *Pongamia glabra* and *Milletia pinnata*.

In an embodiment, the cosmetic ingredient according to the invention is characterized in that said extract of karanja oil is extracted from the species *Milletia pinnata*.

In an embodiment, the cosmetic ingredient according to the invention is characterized in that the mass percentage in said at least one solvent in said solution is from 20% to 60%.

In an embodiment, the cosmetic ingredient according to the invention is characterized in that the mass percentage of said at least one solvent in said solution is from 40% to 60%.

In an embodiment, the cosmetic ingredient according to the invention is characterized in that the mass percentage of said at least one solvent in said solution is approximately 50%.

In an embodiment, the cosmetic ingredient according to the invention is characterized in that the mass percentage of pongamol in said solution is greater than 1.30%.

In an embodiment, the cosmetic ingredient according to the invention is characterized in that the mass percentage of pongamol in said solution is greater than 1.20%.

In an embodiment, the cosmetic ingredient according to the invention is characterized in that the mass percentage of karanjin in said solution is less than 6%.

In an embodiment, the cosmetic ingredient according to the invention is characterized in that the mass percentage of karanjin in said solution is less than 5%.

In an embodiment, the cosmetic ingredient according to the invention is characterized in that the mass percentage of karanjin in said solution is less than 4.5%.

In an embodiment, the cosmetic ingredient according to the invention is characterized in that the mass percentage of karanjin in said solution is less than 4.3%.

In an embodiment, the cosmetic ingredient according to the invention is characterized in that the $m_{pongamol}/m_{karanjin}$ ratio in said solution is greater than 0.5.

In an embodiment, the cosmetic ingredient according to the invention is characterized in that the $m_{pongamol}/m_{karanjin}$ ratio in said solution is greater than 0.55.

The invention also relates to a process of selective precipitation of pongamol (CAS 484-33-3) in a karanja oil comprising pongamol (CAS 484-33-3) and karanjin (CAS 521-88-0), characterized in that it comprises:

1) at least one step of addition to said at least one karanja oil of at least one solvent selected from the group of the diesters having the following formula (I), or mixtures thereof:

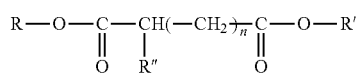

Formula (I)

in which:

n is from 0 to 19;

R and R', which may be identical or different, are alkyls derived from an esterification by a linear or branched alcohol of molecular formula $C_xH_{2x+2}O$, x being from 1 to 30, preferably from 1 to 20, preferably from 1 to 10.

R" is either a hydrogen atom or a $C_1$-$C_3$ alkyl group.

said addition having the effect of forming a light phase in the form of a solution and a heavy phase in the form of precipitate; and 2) at least one step of separation of the two phases obtained.

In an embodiment, the process according to the invention is characterized in that the extraction yield of said karanjin in said light phase in the form of a solution is less than 50%.

In an embodiment, the process according to the invention is characterized in that the extraction yield of said pongamol in said light phase in the form of a solution is greater than 60%.

In an embodiment, the process according to the invention is characterized in that it results in a multiplication of the $m_{pongamol}/m_{karanjin}$ mass ratio by a factor of more than 2.

In an embodiment, the process according to the invention is characterized in that, during said step 1), the mass proportion of said at least one solvent introduced into said at least one karanja oil is from 60/40 to 20/80.

In an embodiment, the process according to the invention is characterized in that steps 1) and 2) are carried out at ambient temperature, for example, at approximately 25° C.

In an embodiment, the process according to the invention is characterized in that said karanja oil originates from a species selected from the group consisting of *Pongamia glabra, Pongamia pinnata, Milletia pinnata, Derris indica, Gadelupa pinnata, Pongamia grandifolia, Robinia mitis, Tephrosia purpurea, Tephrosia hamiltoni, Tephrosia falciformis, Tephrosia vogellii* and *Tephrosia lanceolata.*

In an embodiment, the process according to the invention is characterized in that said karanja oil originates from a species selected from the group consisting of *Pongamia glabra* and *Milletia pinnata.*

In an embodiment, the process according to the invention is characterized in that said karanja oil originates from the species *Milletia pinnata.*

In an embodiment, the process according to the invention is characterized in that said karanja oil is a raw oil.

In an embodiment, the process according to the invention is characterized in that it comprises, in addition, at least one preliminary step of deodorization of said at least one karanja oil and/or at least one preliminary step of distillation of said at least one karanja oil, said steps, when they are both present, being capable of being carried out in any order.

In an embodiment, the process according to the invention is characterized in that it includes, in addition:

3) at least one second step of addition to said solution derived from said step 2) of at least one solvent selected from the group of the diesters having the following formula (I), or mixtures thereof:

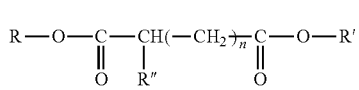

Formula (I)

in which:

n is from 0 to 19;

R and R', which may be identical or different, are alkyls derived from an esterification by a linear or branched alcohol of molecular formula $C_xH_{2x+2}O$, x being from 1 to 30, preferably from 1 to 20, preferably from 1 to 10.

R" is a hydrogen atom or a $C_1$-$C_3$ alkyl group.

said second addition step having the effect of forming a light phase in the form of a solution and a heavy phase in the form of a precipitate; and 4) a second step of separation of the two phases obtained; and in that said at least one solvent of step 3) is identical or different from the at least one solvent of step 1).

In an embodiment, the process according to the invention is characterized in that said at least one solvent is selected from the group consisting of the sebacates (n=7), the adipates (n=3), the succinates (n=1), the dodecanedioates (n=9), the azelates (n=6), the glutarates (n=2), the malonates (n=0), and mixtures thereof.

In an embodiment, the process according to the invention is characterized in that said at least one solvent is selected from the group consisting of the sebacates (n=7).

In an embodiment, the process according to the invention is characterized in that said at least one solvent is diethyl sebacate (CAS 110-40-7).

In an embodiment, the process according to the invention is characterized in that R" is a hydrogen atom.

In an embodiment, the process according to the invention is characterized in that R" is a methyl.

In an embodiment, the process according to the invention is characterized in that x is from 1 to 20.

In an embodiment, the process according to the invention is characterized in that x is from 1 to 10.

In an embodiment, the process according to the invention is characterized in that n is from 1 to 10.

In an embodiment, the process according to the invention is characterized in that R is identical to R'.

In an embodiment, the process according to the invention is characterized in that R is different from R'.

In an embodiment, the process according to the invention is characterized in that said at least one solvent is selected from the group consisting of the sebacates (n=7), the adipates (n=3), the succinates (n=1), the dodecanedioates (n=9), the azelates (n=6), the glutarates (n=2), the malonates (n=0), and mixtures thereof.

In an embodiment, the process according to the invention is characterized in that said at least one solvent is a sebacic acid doubly esterified by two identical or different alcohols, each of the two alcohols being a linear or branched alcohol, or a mixture of isomers in any proportions where appropriate, or a single one of the isomers where appropriate, the alcohol being a $C_1$-$C_{30}$ alcohol, preferably a $C_1$-$C_{20}$ alcohol, preferably a $C_1$-$C_{10}$ alcohol.

In an embodiment, the process according to the invention is characterized in that said at least one solvent is a sebacic acid doubly esterified by two identical or different alcohols, each of the two alcohols being selected from the group consisting of methanol, ethanol, the propanols of molecular formula $C_3H_8O$, the butanols of molecular formula $C_4H_{10}O$, the pentanols of molecular formula $C_5H_{12}O$, the hexanols of molecular formula $C_6H_{14}O$, the heptanols of molecular formula $C_7H_{16}O$, the octanols of molecular formula $C_8H_{18}O$, the nonanols of molecular formula $C_9H_{20}O$, the decanols of molecular formula $C_{10}H_{22}O$, the undecanols of molecular formula $C_{11}H_{24}O$, the dodecanols of molecular formula $C_{12}H_{26}O$, the tridecanols of molecular formula $C_{13}H_{28}O$, the tetradecanols of molecular formula $C_{14}H_{30}O$, the pentadecanols of molecular formula $C_{15}H_{32}O$, the hexadecanols of molecular formula $C_{16}H_{34}O$, the heptadecanols of molecular formula $C_{17}H_{36}O$, the octadecanols of molecular formula $C_{18}H_{38}O$, the nonadecanols of molecular formula $C_{19}H_{40}O$ and the eicosanols of molecular formula $C_{20}H_{42}O$.

In an embodiment, the process according to the invention is characterized in that said at least one solvent is a sebacic acid doubly esterified by two identical or different alcohols, each of the two alcohols being selected from the group consisting of methanol (CAS 67-56-1), ethanol (CAS 64-17-5), propan-1-ol (or n-propanol) (CAS 71-23-8), propan-2-ol (or isopropanol) (CAS 67-63-0), butan-1-ol (or n-butanol) (CAS 71-36-3), (R)-butan-2-ol (CAS 14898-79-4), (S)-butan-2-ol (CAS 4221-99-2), 2-methylpropan-1-ol (CAS 78-83-1), 2-methylpropan-2-ol (CAS 75-65-0), 2-methylpropan-2-ol (CAS 75-65-0), pentan-1-ol (CAS 71-41-0), 3-methylbutan-1-ol (CAS 123-51-3), 2-methylbutan-1-ol (CAS 137-32-6), 2,2-dimethylpropan-1-ol (CAS 75-84-3), pentan-3-ol (CAS 584-02-1), pentan-2-ol (CAS 6032-29-7), 3-methylbutan-2-ol (CAS 598-75-4), 2-methylbutan-2-ol (CAS 75-85-4), hexan-1-ol (CAS 111-27-3), heptan-1-ol (CAS 111-70-6), dodecan-1-ol (CAS 112-53-8), octan-1-ol (CAS 111-87-5), 2-ethylhexan-1-ol (CAS 104-76-7), octadecan-1-ol (CAS 112-92-5), decan-1-ol (CAS 112-30-1) and dodecan-1-ol (CAS 112-53-8).

In an embodiment, the process according to the invention is characterized in that said at least one solvent is selected from the group consisting of dioctyl sebacate (CAS 122-62-3), diethyl sebacate (CAS 110-40-7), dibutyl sebacate (CAS 109-43-3), diisopropyl sebacate (CAS 7491-02-3), and mixtures thereof.

In an embodiment, the process according to the invention is characterized in that said at least one solvent is selected from the group consisting of diethyl sebacate (CAS 110-40-7), dibutyl sebacate (CAS 109-43-3), diisopropyl sebacate (CAS 7491-02-3), and mixtures thereof.

In an embodiment, the process according to the invention is characterized in that said at least one solvent is diethyl sebacate (CAS 110-40-7).

In an embodiment, the process according to the invention is characterized in that said at least one solvent is a sebacic acid doubly esterified by two identical or different alcohols, each of the two alcohols being a linear or branched alcohol, or a mixture of isomers in any proportions where appropriate, or a single one of the isomers where appropriate, the alcohol being a $C_1$-$C_{30}$ alcohol, preferably a $C_1$-$C_{20}$ alcohol, preferably a $C_1$-$C_{10}$ alcohol.

In an embodiment, the process according to the invention is characterized in that said at least one solvent is an adipic acid doubly esterified by two identical or different alcohols, each of the two alcohols being selected from the group consisting of methanol, ethanol, the propanols of molecular formula $C_3H_8O$, the butanols of molecular formula $C_4H_{10}O$, the pentanols of molecular formula $C_5H_{12}O$, the hexanols of molecular formula $C_6H_{14}O$, the heptanols of molecular formula $C_7H_{16}O$, the octanols of molecular formula $C_8H_{18}O$, the nonanols of molecular formula $C_9H_{20}O$, the decanols of molecular formula $C_{10}H_{22}O$, the undecanols of molecular formula $C_{11}H_{24}O$, the dodecanols of molecular formula $C_{12}H_{26}O$, the tridecanols of molecular formula $C_{13}H_{28}O$, the tetradecanols of molecular formula $C_{14}H_{30}O$, the pentadecanols of molecular formula $C_{15}H_{32}O$, the hexadecanols of molecular formula $C_{16}H_{34}O$, the heptadecanols of molecular formula $C_{17}H_{36}O$, the octadecanols of molecular formula $C_{18}H_{38}O$, the nonadecanols of molecular formula $C_{19}H_{40}O$ and the eicosanols of molecular formula $C_{20}H_{42}O$.

In an embodiment, the process according to the invention is characterized in that said at least one solvent is an adipic acid doubly esterified by two identical or different alcohols, each of the two alcohols being selected from the group consisting of methanol (CAS 67-56-1), ethanol (CAS 64-17-5), propan-1-ol (or n-propanol) (CAS 71-23-8), propan-2-ol (or isopropanol) (CAS 67-63-0), butan-1-ol (or n-butanol) (CAS 71-36-3), (R)-butan-2-ol (CAS 14898-79-4), (S)-butan-2-ol (CAS 4221-99-2), 2-methylpropan-1-ol (CAS 78-83-1), 2-methylpropan-2-ol (CAS 75-65-0), 2-methylpropan-2-ol (CAS 75-65-0), pentan-1-ol (CAS 71-41-0), 3-methylbutan-1-ol (CAS 123-51-3), 2-methylbutan-1-ol (CAS 137-32-6), 2,2-dimethylpropan-1-ol (CAS 75-84-3), pentan-3-ol (CAS 584-02-1), pentan-2-ol (CAS 6032-29-7), 3-methylbutan-2-ol (CAS 598-75-4), 2-methylbutan-2-ol (CAS 75-85-4), hexan-1-ol (CAS 111-27-3), heptan-1-ol (CAS 111-70-6), dodecan-1-ol (CAS 112-53-8), octan-1-ol (CAS 111-87-5), 2-ethylhexan-1-ol (CAS 104-76-7), octadecan-1-ol (CAS 112-92-5), decan-1-ol (CAS 112-30-1) and dodecan-1-ol (CAS 112-53-8).

In an embodiment, the process according to the invention is characterized in that said at least one solvent is selected from the group consisting of dihexyl adipate (CAS 2091-24-9), diisostearyl adipate (CAS 62479-36-1), dicapryl adipate (CAS 108-63-4), di-C12-15 alkyl adipate, ditridecyl adipate (CAS 16958-92-2), dicetyl adipate (CAS 26720-21-8), diisopropyl adipate (CAS 6938-94-9), diisobutyl adipate (CAS 141-04-8), diethylhexyl adipate (CAS 103-23-1), diisooctyl adipate (CAS 1330-86-5), diisononyl adipate (CAS 33703-08-1), diisodecyl adipate (CAS 27178-16-1), diethyl adipate (CAS 141-28-6), dimethyl adipate (CAS 627-93-0), dihexyldecyl adipate (CAS 57533-90-1), diheptylundecyl adipate (CAS 155613-91-5), dipropyl adipate (CAS 106-19-4), dioctyldodecyl adipate (CAS 85117-94-8), dibutyl adipate (CAS 105-99-7), diisocetyl adipate (CAS 57533-90-1), dioctyl adipate (CAS 123-79-5), and mixtures thereof.

In an embodiment, the process according to the invention is characterized in that said at least one solvent is selected from the group consisting of diisopropyl adipate (CAS 6938-94-9), dibutyl adipate (CAS 105-99-7), dioctyl adipate (CAS 123-79-5), and mixtures thereof.

In an embodiment, the process according to the invention is characterized in that said at least one solvent is a sebacic acid doubly esterified by two identical or different alcohols, each of the two alcohols being a linear or branched alcohol, or a mixture of isomers in any proportions where appropriate, or a single one of the isomers where appropriate, the alcohol being a $C_1$-$C_{30}$ alcohol, preferably a $C_1$-$C_{20}$ alcohol, preferably a $C_1$-$C_{10}$ alcohol.

In an embodiment, the process according to the invention is characterized in that said at least one solvent is a succinic acid doubly esterified by two identical or different alcohols, each of the two alcohols being selected from the group consisting of methanol, ethanol, the propanols of molecular formula $C_3H_8O$, the butanols of molecular formula $C_4H_{10}O$, the pentanols of molecular formula $C_5H_{12}O$, the hexanols of molecular formula $C_6H_{14}O$, the heptanols of molecular formula $C_7H_{16}O$, the octanols of molecular formula $C_8H_{18}O$, the nonanols of molecular formula $C_9H_{20}O$, the decanols of molecular formula $C_{10}H_{22}O$, the undecanols of molecular formula $C_{11}H_{24}O$, the dodecanols of molecular formula $C_{12}H_{26}O$, the tridecanols of molecular formula $C_{13}H_{28}O$, the tetradecanols of molecular formula $C_{14}H_{30}O$, the pentadecanols of molecular formula $C_{15}H_{32}O$, the hexadecanols of molecular formula $C_{16}H_{34}O$, the heptadecanols of molecular formula $C_{17}H_{36}O$, the octadecanols of molecular formula $C_{18}H_{38}O$, the nonadecanols of molecular formula $C_{19}H_{40}O$ and the eicosanols of molecular formula $C_{20}H_{42}O$.

In an embodiment, the process according to the invention is characterized in that said at least one solvent is a succinic acid doubly esterified by two identical or different alcohols, each of the two alcohols being selected from the group consisting of methanol (CAS 67-56-1), ethanol (CAS 64-17-5), propan-1-ol (or n-propanol) (CAS 71-23-8), propan-2-ol (or isopropanol) (CAS 67-63-0), butan-1-ol (or n-butanol) (CAS 71-36-3), (R)-butan-2-ol (CAS 14898-79-4), (S)-butan-2-ol (CAS 4221-99-2), 2-methylpropan-1-ol (CAS 78-83-1), 2-methylpropan-2-ol (CAS 75-65-0), 2-methylpropan-2-ol (CAS 75-65-0), pentan-1-ol (CAS 71-41-0), 3-methylbutan-1-ol (CAS 123-51-3), 2-methylbutan-1-ol (CAS 137-32-6), 2,2-dimethylpropan-1-ol (CAS 75-84-3), pentan-3-ol (CAS 584-02-1), pentan-2-ol (CAS 6032-29-7), 3-methylbutan-2-ol (CAS 598-75-4), 2-methylbutan-2-ol (CAS 75-85-4), hexan-1-ol (CAS 111-27-3), heptan-1-ol (CAS 111-70-6), dodecan-1-ol (CAS 112-53-8), octan-1-ol (CAS 111-87-5), 2-ethylhexan-1-ol (CAS 104-76-7), octadecan-1-ol (CAS 112-92-5), decan-1-ol (CAS 112-30-1) and dodecan-1-ol (CAS 112-53-8).

In an embodiment, the process according to the invention is characterized in that said at least one solvent is selected from the group consisting of dodecyl succinate (CAS 10595-82-1), dimethyl succinate (CAS 106-65-0), diethyl succinate (CAS 123-25-1), dicapryl succinate (CAS 14491-66-8), dicetearyl succinate (CAS 93280-98-9), diisobutyl succinate (CAS 925-06-4), diethylhexyl succinate (CAS 2915-57-3), and mixtures thereof.

In an embodiment, the process according to the invention is characterized in that said at least one solvent is diethylhexyl succinate (CAS 2915-57-3).

In an embodiment, the process according to the invention is characterized in that said at least one solvent is a 2-methylsuccinic acid doubly esterified by two identical or different alcohols, each of the two alcohols being a linear or branched alcohol, or a mixture of isomers in any proportions where appropriate, or a single one of the isomers where appropriate, the alcohol being a $C_1$-$C_{30}$ alcohol, preferably a $C_1$-$C_{20}$ alcohol, preferably a $C_1$-$C_{10}$ alcohol.

In an embodiment, the process according to the invention is characterized in that said at least one solvent is a 2-methylsuccinic acid doubly esterified by two identical or different alcohols, each of the two alcohols being selected from the group consisting of methanol, ethanol, the propanols of molecular formula $C_3H_8O$, the butanols of molecular formula $C_4H_{10}O$, the pentanols of molecular formula $C_5H_{12}O$, the hexanols of molecular formula $C_6H_{14}O$, the heptanols of molecular formula $C_7H_{16}O$, the octanols of molecular formula $C_8H_{18}O$, the nonanols of molecular formula $C_9H_{20}O$, the decanols of molecular formula $C_{10}H_{22}O$, the undecanols of molecular formula $C_{11}H_{24}O$, the dodecanols of molecular formula $C_{12}H_{26}O$, the tridecanols of molecular formula $C_{13}H_{28}O$, the tetradecanols of molecular formula $C_{14}H_{30}O$, the pentadecanols of molecular formula $C_{15}H_{32}O$, the hexadecanols of molecular formula $C_{16}H_{34}O$, the heptadecanols of molecular formula $C_{17}H_{36}O$, the octadecanols of molecular formula $C_{18}H_{38}O$, the nonadecanols of molecular formula $C_{19}H_{40}O$ and the eicosanols of molecular formula $C_{20}H_{42}O$.

In an embodiment, the process according to the invention is characterized in that said at least one solvent is a 2-methylsuccinic acid doubly esterified by two identical or different alcohols, each of the two alcohols being selected from the group consisting of methanol (CAS 67-56-1), ethanol (CAS 64-17-5), propan-1-ol (or n-propanol) (CAS 71-23-8), propan-2-ol (or isopropanol) (CAS 67-63-0), butan-1-ol (or n-butanol) (CAS 71-36-3), (R)-butan-2-ol (CAS 14898-79-4), (S)-butan-2-ol (CAS 4221-99-2), 2-methylpropan-1-ol (CAS 78-83-1), 2-methylpropan-2-ol (CAS 75-65-0), 2-methylpropan-2-ol (CAS 75-65-0), pentan-1-ol (CAS 71-41-0), 3-methylbutan-1-ol (CAS 123-51-3), 2-methylbutan-1-ol (CAS 137-32-6), 2,2-dimethylpropan-1-ol (CAS 75-84-3), pentan-3-ol (CAS 584-02-1), pentan-2-ol (CAS 6032-29-7), 3-methylbutan-2-ol (CAS 598-75-4), 2-methylbutan-2-ol (CAS 75-85-4), hexan-1-ol (CAS 111-27-3), heptan-1-ol (CAS 111-70-6), dodecan-1-ol (CAS 112-53-8), octan-1-ol (CAS 111-87-5), 2-ethylhexan-1-ol (CAS 104-76-7), octadecan-1-ol (CAS 112-92-5), decan-1-ol (CAS 112-30-1) and dodecan-1-ol (CAS 112-53-8).

In an embodiment, the process according to the invention is characterized in that said at least one solvent is selected from the group consisting of diethyl 2-methylsuccinate (CAS 4676-51-1), 1-ethyl and 4-methyl 2-methylsuccinate (CAS 204125-41-7), 1-methyl and 4-methyl 2-methylsuccinate (CAS 606491-29-6), dipropyl 2-methylsuccinate (CAS 56108-32-8), diisopropyl 2-methylsuccinate (CAS 75906-62-6), 1-butyl and 4-methyl 2-methylsuccinate (CAS 878209-18-8), di(2-methylpropyl) 2-methylsuccinate (CAS 18447-89-7), 1-pentyl and 4-methyl 2-methylsuccinate (CAS 204125-40-6), 1-methyl and 4-hexyl 2-methylsuccinate (CAS 214280-22-5), di(1-methylpropyl) 2-methylsuccinate (CAS 57983-31-0), di(1,1-dimethylethyl) 2-methylsuccinate (CAS 108763-17-3), dipentyl 2-methylsuccinate (CAS 56108-33-9), dihexyl 2-methylsuccinate (CAS 32774-96-2), diheptyl 2-methylsuccinate (CAS 51191-78-7), 1-methyl and 4-dodecyl 2-methylsuccinate (CAS 214280-27-0), dioctyl 2-methylsuccinate (CAS 131787-12-7), 1-methyl and 4-octadecyl 2-methylsuccinate, didecyl 2-methylsuccinate, didodecyl or lauryl 2-methylsuccinate, decanyl 2-methylsuccinate, 2-ethylhexanyl 2-methylsuccinate, the isomers and isomer mixtures thereof, and mixtures thereof.

In an embodiment, the process according to the invention is characterized in that said at least one solvent is a sebacic acid doubly esterified by two identical or different alcohols, each of the two alcohols being a linear or branched alcohol, or a mixture of isomers in any proportions where appropriate, or a single one of the isomers where appropriate, the alcohol being a $C_1$-$C_{30}$ alcohol, preferably a $C_1$-$C_{20}$ alcohol, preferably a $C_1$-$C_{10}$ alcohol.

In an embodiment, the process according to the invention is characterized in that said at least one solvent is a dodecanedioic acid doubly esterified by two identical or different alcohols, each of the two alcohols being selected from the group consisting of methanol, ethanol, the propanols of molecular formula $C_3H_8O$, the butanols of molecular formula $C_4H_{10}O$, the pentanols of molecular formula $C_5H_{12}O$, the hexanols of molecular formula $C_6H_{14}O$, the heptanols of molecular formula $C_7H_{16}O$, the octanols of molecular formula $C_8H_{18}O$, the nonanols of molecular formula $C_9H_{20}O$, the decanols of molecular formula $C_{10}H_{22}O$, the undecanols of molecular formula $C_{11}H_{24}O$, the dodecanols of molecular formula $C_{12}H_{26}O$, the tridecanols of molecular formula $C_{13}H_{28}O$, the tetradecanols of molecular formula $C_{14}H_{30}O$, the pentadecanols of molecular formula $C_{15}H_{32}O$, the hexadecanols of molecular formula $C_{16}H_{34}O$, the heptadecanols of molecular formula $C_{17}H_{36}O$, the octadecanols of molecular formula $C_{18}H_{38}O$, the nonadecanols of molecular formula $C_{19}H_{40}O$ and the eicosanols of molecular formula $C_{20}H_{42}O$.

In an embodiment, the process according to the invention is characterized in that said at least one solvent is a dodecanedioic acid doubly esterified by two identical or different alcohols, each of the two alcohols being selected from the group consisting of methanol (CAS 67-56-1), ethanol (CAS 64-17-5), propan-1-ol (or n-propanol) (CAS 71-23-8), propan-2-ol (or isopropanol) (CAS 67-63-0), butan-1-ol (or n-butanol) (CAS 71-36-3), (R)-butan-2-ol (CAS 14898-79-4), (S)-butan-2-ol (CAS 4221-99-2), 2-methylpropan-1-ol (CAS 78-83-1), 2-methylpropan-2-ol (CAS 75-65-0), 2-methylpropan-2-ol (CAS 75-65-0), pentan-1-ol (CAS 71-41-0), 3-methylbutan-1-ol (CAS 123-51-3), 2-methylbutan-1-ol (CAS 137-32-6), 2,2-dimethylpropan-1-ol (CAS 75-84-3), pentan-3-ol (CAS 584-02-1), pentan-2-ol (CAS 6032-29-7), 3-methylbutan-2-ol (CAS 598-75-4), 2-methylbutan-2-ol (CAS 75-85-4), hexan-1-ol (CAS 111-27-3), heptan-1-ol (CAS 111-70-6), dodecan-1-ol (CAS 112-53-8), octan-1-ol (CAS 111-87-5), 2-ethylhexan-1-ol (CAS 104-76-7), octadecan-1-ol (CAS 112-92-5), decan-1-ol (CAS 112-30-1) and dodecan-1-ol (CAS 112-53-8).

In an embodiment, the process according to the invention is characterized in that said at least one solvent is selected from the group consisting of dioctyldodecyl dodecanedioate (CAS 129423-55-8), diisocetyl dodecanedioate (CAS 131252-83-0), and mixtures thereof.

In an embodiment, the process according to the invention is characterized in that said at least one solvent is a sebacic acid doubly esterified by two identical or different alcohols, each of the two alcohols being a linear or branched alcohol, or a mixture of isomers in any proportions where appropriate, or a single one of the isomers where appropriate, the alcohol being a $C_1$-$C_{30}$ alcohol, preferably a $C_1$-$C_{20}$ alcohol, preferably a $C_1$-$C_{10}$ alcohol.

In an embodiment, the process according to the invention is characterized in that said at least one solvent is an azelaic acid doubly esterified by two identical or different alcohols, each of the two alcohols being selected from the group consisting of methanol, ethanol, the propanols of molecular formula $C_3H_8O$, the butanols of molecular formula $C_4H_{10}O$, the pentanols of molecular formula $C_5H_{12}O$, the hexanols of molecular formula $C_6H_{14}O$, the heptanols of molecular formula $C_7H_{16}O$, the octanols of molecular formula $C_8H_{18}O$, the nonanols of molecular formula $C_9H_{20}O$, the decanols of molecular formula $C_{10}H_{22}O$, the undecanols of molecular formula $C_{11}H_{24}O$, the dodecanols of molecular formula $C_{12}H_{26}O$, the tridecanols of molecular formula $C_{13}H_{28}O$, the tetradecanols of molecular formula $C_{14}H_{30}O$, the pentadecanols of molecular formula $C_{15}H_{32}O$, the hexadecanols of molecular formula $C_{16}H_{34}O$, the heptadecanols of molecular formula $C_{17}H_{36}O$, the octadecanols of molecular formula $C_{18}H_{38}O$, the nonadecanols of molecular formula $C_{19}H_{40}O$ and the eicosanols of molecular formula $C_{20}H_{42}O$.

In an embodiment, the process according to the invention is characterized in that said at least one solvent is an azelaic acid doubly esterified by two identical or different alcohols, each of the two alcohols being selected from the group consisting of methanol (CAS 67-56-1), ethanol (CAS 64-17-5), propan-1-ol (or n-propanol) (CAS 71-23-8), propan-2-ol (or isopropanol) (CAS 67-63-0), butan-1-ol (or n-butanol) (CAS 71-36-3), (R)-butan-2-ol (CAS 14898-79-4), (S)-butan-2-ol (CAS 4221-99-2), 2-methylpropan-1-ol (CAS 78-83-1), 2-methylpropan-2-ol (CAS 75-65-0), 2-methylpropan-2-ol (CAS 75-65-0), pentan-1-ol (CAS 71-41-0), 3-methylbutan-1-ol (CAS 123-51-3), 2-methylbutan-1-ol (CAS 137-32-6), 2,2-dimethylpropan-1-ol (CAS 75-84-3), pentan-3-ol (CAS 584-02-1), pentan-2-ol (CAS 6032-29-7), 3-methylbutan-2-ol (CAS 598-75-4), 2-methylbutan-2-ol (CAS 75-85-4), hexan-1-ol (CAS 111-27-3), heptan-1-ol (CAS 111-70-6), dodecan-1-ol (CAS 112-53-8), octan-1-ol (CAS 111-87-5), 2-ethylhexan-1-ol (CAS 104-76-7), octadecan-1-ol (CAS 112-92-5), decan-1-ol (CAS 112-30-1) and dodecan-1-ol (CAS 112-53-8).

In an embodiment, the process according to the invention is characterized in that said at least one solvent is selected from the group consisting of dimethyl azelate (CAS 1732-10-1), di(2-ethylhexyl) azelate, and mixtures thereof.

In an embodiment, the process according to the invention is characterized in that said at least one solvent is a sebacic acid doubly esterified by two identical or different alcohols, each of the two alcohols being a linear or branched alcohol, or a mixture of isomers in any proportions where appropriate, or a single one of the isomers where appropriate, the alcohol being a $C_1$-$C_{30}$ alcohol, preferably a $C_1$-$C_{20}$ alcohol, preferably a $C_1$-$C_{10}$ alcohol.

In an embodiment, the process according to the invention is characterized in that the at least one solvent is a glutaric acid doubly esterified by two identical or different alcohols, each of the two alcohols being selected from the group consisting of methanol, ethanol, the propanols of molecular formula $C_3H_8O$, the butanols of molecular formula $C_4H_{10}O$, the pentanols of molecular formula $C_5H_{12}O$, the hexanols of molecular formula $C_6H_{14}O$, the heptanols of molecular formula $C_7H_{16}O$, the octanols of molecular formula $C_8H_{18}O$, the nonanols of molecular formula $C_9H_{20}O$, the decanols of molecular formula $C_{10}H_{22}O$, the undecanols of molecular formula $C_{11}H_{24}O$, the dodecanols of molecular formula $C_{12}H_{26}O$, the tridecanols of molecular formula $C_{13}H_{28}O$, the tetradecanols of molecular formula $C_{14}H_{30}O$, the pentadecanols of molecular formula $C_{15}H_{32}O$, the hexadecanols of molecular formula $C_{16}H_{34}O$, the heptadecanols of molecular formula $C_{17}H_{36}O$, the octadecanols of molecular formula $C_{18}H_{38}O$, the nonadecanols of molecular formula $C_{19}H_{40}O$ and the eicosanols of molecular formula $C_{20}H_{42}O$.

In an embodiment, the process according to the invention is characterized in that said at least one solvent is a glutaric acid doubly esterified by two identical or different alcohols, each of the two alcohols being selected from the group consisting of methanol (CAS 67-56-1), ethanol (CAS 64-17-5), propan-1-ol (or n-propanol) (CAS 71-23-8), propan-2-ol (or isopropanol) (CAS 67-63-0), butan-1-ol (or n-butanol) (CAS 71-36-3), (R)-butan-2-ol (CAS 14898-79-4), (S)-butan-2-ol (CAS 4221-99-2), 2-methylpropan-1-ol (CAS 78-83-1), 2-methylpropan-2-ol (CAS 75-65-0), 2-methylpropan-2-ol (CAS 75-65-0), pentan-1-ol (CAS 71-41-0), 3-methylbutan-1-ol (CAS 123-51-3), 2-methylbutan-1-ol (CAS 137-32-6), 2,2-dimethylpropan-1-ol (CAS 75-84-3), pentan-3-ol (CAS 584-02-1), pentan-2-ol (CAS 6032-29-7), 3-methylbutan-2-ol (CAS 598-75-4), 2-methylbutan-2-ol (CAS 75-85-4), hexan-1-ol (CAS 111-27-3), heptan-1-ol (CAS 111-70-6), dodecan-1-ol (CAS 112-53-8), octan-1-ol (CAS 111-87-5), 2-ethylhexan-1-ol (CAS 104-76-7), octadecan-1-ol (CAS 112-92-5), decan-1-ol (CAS 112-30-1) and dodecan-1-ol (CAS 112-53-8).

In an embodiment, the process according to the invention is characterized in that said at least one solvent is selected from the group consisting of dimethyl glutarate (CAS 1119-40-0), diisobutyl glutarate (CAS 71195-64-7), diisostearyl glutarate, dimethyl 2-methylglutarate (CAS 14035-94-0), and mixtures thereof.

In an embodiment, the process according to the invention is characterized in that said at least one solvent is a sebacic acid doubly esterified by two identical or different alcohols, each of the two alcohols being a linear or branched alcohol, or a mixture of isomers in any proportions where appropriate, or a single one of the isomers where appropriate, the alcohol being a $C_1$-$C_{30}$ alcohol, preferably a $C_1$-$C_{20}$ alcohol, preferably a $C_1$-$C_{10}$ alcohol.

In an embodiment, the process according to the invention is characterized in that said at least one solvent is a malonic acid doubly esterified by two identical or different alcohols, each of the two alcohols being selected from the group consisting of methanol, ethanol, the propanols of molecular formula $C_3H_8O$, the butanols of molecular formula $C_4H_{10}O$, the pentanols of molecular formula $C_5H_{12}O$, the hexanols of molecular formula $C_6H_{14}O$, the heptanols of molecular formula $C_7H_{16}O$, the octanols of molecular formula $C_8H_{18}O$, the nonanols of molecular formula $C_9H_{20}O$, the decanols of molecular formula $C_{10}H_{22}O$, the undecanols of molecular formula $C_{11}H_{24}O$, the dodecanols of molecular formula $C_{12}H_{26}O$, the tridecanols of molecular formula $C_{13}H_{28}O$, the tetradecanols of molecular formula $C_{14}H_{30}O$, the pentadecanols of molecular formula $C_{15}H_{32}O$, the hexadecanols of molecular formula $C_{16}H_{34}O$, the heptadecanols of molecular formula $C_{17}H_{36}O$, the octadecanols of molecular formula $C_{18}H_{38}O$, the nonadecanols of molecular formula $C_{19}H_{40}O$ and the eicosanols of molecular formula $C_{20}H_{42}O$.

In an embodiment, the process according to the invention is characterized in that said at least one solvent is a malonic acid doubly esterified by two identical or different alcohols, each of the two alcohols being selected from the group consisting of methanol (CAS 67-56-1), ethanol (CAS 64-17-5), propan-1-ol (or n-propanol) (CAS 71-23-8), propan-2-ol (or isopropanol) (CAS 67-63-0), butan-1-ol (or n-butanol) (CAS 71-36-3), (R)-butan-2-ol (CAS 14898-79-4), (S)-butan-2-ol (CAS 4221-99-2), 2-methylpropan-1-ol (CAS 78-83-1), 2-methylpropan-2-ol (CAS 75-65-0), 2-methylpropan-2-ol (CAS 75-65-0), pentan-1-ol (CAS 71-41-0), 3-methylbutan-1-ol (CAS 123-51-3), 2-methylbutan-1-ol (CAS 137-32-6), 2,2-dimethylpropan-1-ol (CAS 75-84-3), pentan-3-ol (CAS 584-02-1), pentan-2-ol (CAS 6032-29-7), 3-methylbutan-2-ol (CAS 598-75-4), 2-methylbutan-2-ol (CAS 75-85-4), hexan-1-ol (CAS 111-27-3), heptan-1-ol (CAS 111-70-6), dodecan-1-ol (CAS 112-53-8), octan-1-ol (CAS 111-87-5), 2-ethylhexan-1-ol (CAS 104-76-7), octadecan-1-ol (CAS 112-92-5), decan-1-ol (CAS 112-30-1) and dodecan-1-ol (CAS 112-53-8).

In an embodiment, the process according to the invention is characterized in that said at least one solvent is diethyl malonate (CAS 105-53-3).

The invention also relates to a cosmetic formulation, characterized in that it comprises:
at least one cosmetic ingredient according to the invention as described above; and
at least one cosmetically acceptable vehicle.

The cosmetic formulation according to the invention can moreover comprise one or more organic or mineral additional sunscreens.

Among the hydrophilic or lipophilic organic filters which are active in the UV-A and/or UV-B, the following are mentioned as examples: the cinnamic derivatives, the salicylic derivatives, the camphor derivatives, the triazine derivatives, the benzophenone derivatives, the dibenzoylmethane derivatives, the β,β-diphenyl acrylate derivatives, the p-aminobenzoic acid derivatives, the polymer filters and the silicone filters.

Among the mineral filters, the following can be mentioned as examples: photoprotective agents which act by physical blocking (reflection and/or scattering) of UV radiation and which are pigments or nanopigments of which the average primary particle size is from 5 nm to 500 nm, preferably from 100 to 250 nm. These pigments or nanopigments are coated or uncoated metal oxides, for example, nanopigments made of titanium oxide, iron oxide, zinc oxide, zirconium oxide or cerium oxide. If they are coated, the coating agents are, for example, alumina and/or aluminum stearate.

The cosmetic formulation according to the invention can also comprise derivatives of tyrosine or dihydroxyacetone (DHA) which are artificial skin tanning and/or browning agents (self-tanning agents).

The cosmetic formulation according to the invention can moreover comprise conventional cosmetic adjuvants used as formulation supports and constituents selected from the fatty substances, the organic solvents, the ionic or nonionic thickeners, the softeners, the opacifiers, the emollients, the silicones, the anti-foaming agents, the surfactants, the fillers, the sequestrants, the polymers, the propellants, the alkalizing or acidifying agents, the dyes, or any other ingredient conventionally used in cosmetics.

The fatty substances can consist of an oil or a wax or mixtures thereof, and they also comprise fatty acids, fatty alcohols and fatty acid esters. The oils can be selected from the animal, plant, mineral or synthetic oils and, in particular, from vaseline oil, paraffin oil, silicone oil, which may be volatile or nonvolatile, the isoparaffins, the poly-α-olefins, the fluorinated and perfluorinated oils. Similarly, the waxes can be selected from the animal, fossil, plant, mineral or synthetic waxes which are known per se.

Among the organic solvents, one can mention the alcohols and lower polyols.

In particular, the thickeners can be selected from the cross-linked polyacrylic acids, the guar gums, and modified or unmodified celluloses such as hydroxypropylated guar gum, methylhydroxyethylcellulose and hydroxypropyl methylcellulose.

The cosmetic formulation according to the invention can moreover comprise conventional cosmetic adjuvants used as agents, namely preservative or stabilizing agents such as the antioxidants or the stabilizers.

In addition, it can comprise hydrating agents, vitamins or perfumes.

The cosmetic formulation according to the invention can be in the form of a simple or complex emulsion (O/W, W/O, O/W/O or W/O/W) such as a cream, a milk, a gel or a cream-gel and it can be prepared according to the techniques which are well known to the person skilled in the art, in particular the techniques intended for preparing oil-in-water (O/W) or water-in-oil (W/O) emulsions.

It can optionally be packaged in an aerosol and be in the form of a foam or spray.

The cosmetic formulation according to the invention can be used as protective composition for the human epidermis or for hair against ultraviolet radiation, as a sunscreen composition or as makeup product.

The invention also relates to the use of a cosmetic formulation according to the invention as described above, as a solar cosmetic formulation.

The invention also relates to the use of a cosmetic formulation according to the invention as described above, as an anti-wrinkle cosmetic formulation.

EXAMPLES

Example 1: Determination of the Mass Percentage of Karanjin and of Pongamol by Liquid Phase Chromatography In all the following examples, the mass percentages of pongamol and of karanjin are measured by HPLC according to a conventional method.

The column used is a Gemini NX-C18 column with reference 00G-4454-50, Phenomenex of which the characteristics are 250×4.6 mm, 5 µm, 110 Å.

The reagents used are the following:

TABLE 1

| Reagents | CAS number | Supplier | Quality, reference |
|---|---|---|---|
| Water | 7732-18-5 | VWR | HiPerSolv |
| Formic acid | 64-18-6 | Aldrich | — |
| Acetonitrile | 75-05-8 | VWR | HiPerSolv |
| Karanjin | 521-88-0 | Chromadex | ASB-00011275-010 |
| Pongamol | 484-33-3 | Biosynthis | nd |
| Dimethyl sulfoxide | 67-68-5 | Aldrich | — |

The analytical conditions are the following:

TABLE 2

| Parameters | Set values | | |
|---|---|---|---|
| Injector | Ambient temperature | | |
| Detector | UV $\lambda = 250$ nm | | |
| Oven | 25° C. | | |
| Flow rate | 1.0 mL/min | | |
| Mobile phase | Pump A: Acidified water (0.1% of formic acid) Pump B: Acetonitrile | | |
| | t (min) | % Acidified water | % ACN |
| Linear elution gradient | 0 | 95 | 5 |
| | 42 | 0 | 100 |
| | 45 | 95 | 5 |
| | 50 | 95 | 5 |
| Duration of the analysis | 50 min | | |
| Volume injected | 10 µL | | |

The calibration was carried out using a stock solution comprising 14.4 mg of raw karanjin standard (p=95.7%) and 33.4 mg of raw pongamol (p=90.0%) 50 mL of DMSO.

The preparation of the series was carried out with DMSO.

The retention times are the following:

TABLE 3

| Compounds | Retention time |
|---|---|
| Karanjin | 28.8 min |
| Pongamol | 33.4 min |

The chromatogram of a calibration solution is given in FIG. 1.

Figure 2:
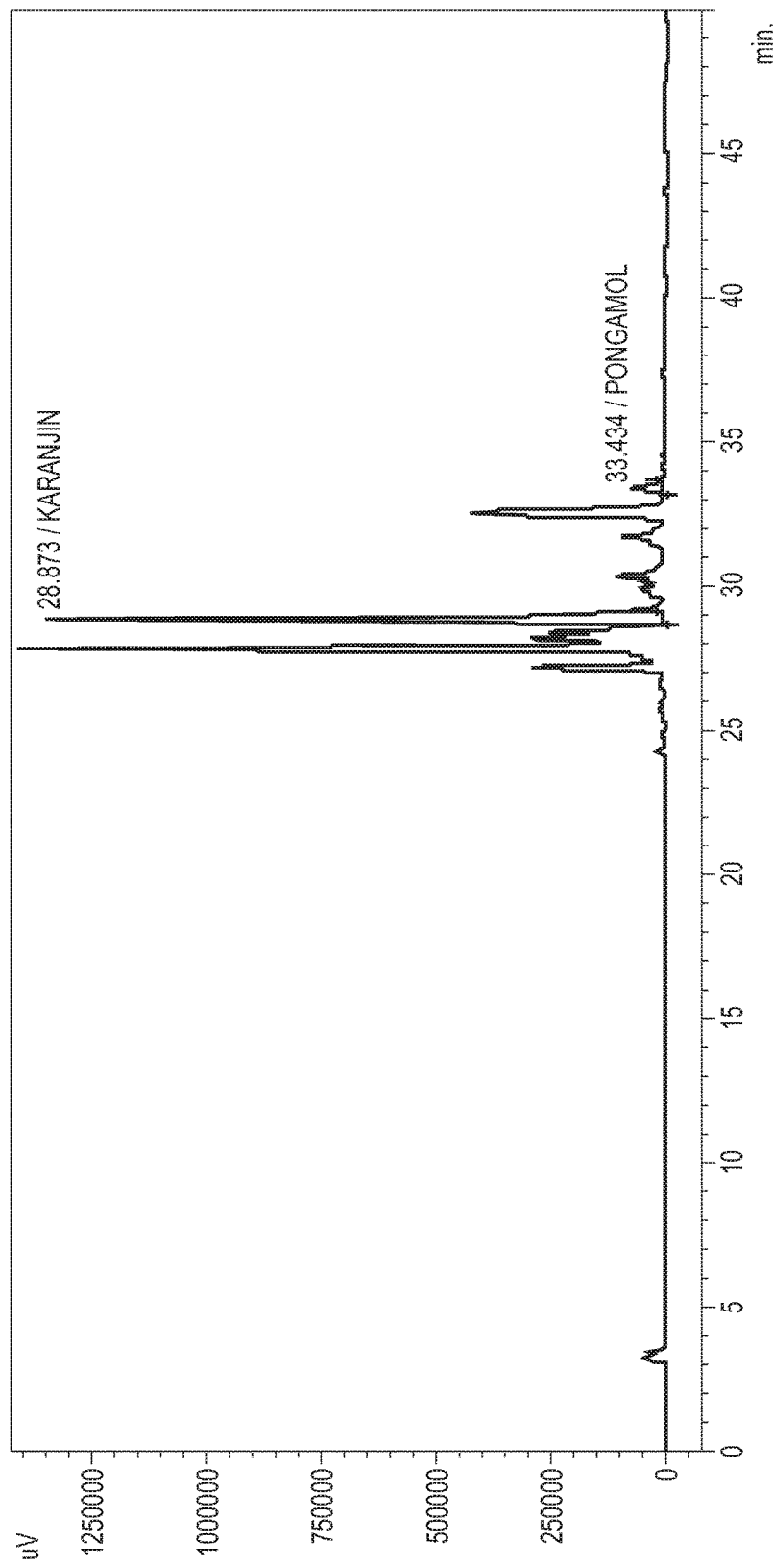
FIG. 2 is a chromatogram of a sample of karanja oil.

The chromatogram of a sample of karanja oil is given in FIG. 2.

The software LC Solutions® makes it possible to determine the concentration (mg/mL) of karanjin and pongamol.

Example 2: Process According to the Invention

A karanja oil which has been subjected to a removal of mucilage and a deodorization, having the following concentrations of pongamol and karanjin, is used:

TABLE 4

| Acid index (mg KOH/g) | 6 |
|---|---|
| Pongamol mass percentage (%) | 1.00 |
| Karanjin mass percentage (%) | 2.5 |
| Pongamol/karanjin ratio | 0.40 |

Step 1: Molecular Distillation

A molecular distillation step is carried out using a KDL5 apparatus with the following conditions: distillation temperature 170° C., vacuum $10^{-2}$ mbar, feed set at 250 mL/h.

The mass balance of the distillation is given below:

TABLE 5

| Heavy phase (%) | 91 |
|---|---|
| Light phase (%) | 9 |

The light distillation phase is then characterized:

TABLE 6

| Acid index (mg KOH/g) | 70.0 |
|---|---|
| Pongamol mass percentage (%) | 10.45 |
| Karanjin mass percentage (%) | 14.8 |
| $m_{pongamol}/m_{karanjin}$ ratio | 0.71 |

Step 2: Precipitation of Karanjin

An identical mass of dimethyl sebacate (CAS 110-40-7) is added to the karanja oil which has been subjected to the molecular distillation (the light distillation phase) (proportions 50/50).

The mixture is stirred for 24 h at 15° C. A precipitate forms. The suspension obtained is then filtered through an 11 µm filter.

The balance of the precipitation is given below:

TABLE 7

| Light phase (supernatant) (%) | 89.7 |
|---|---|
| Heavy phase (precipitate) (%) | 10.3 |

The pongamol and karanjin contents in the light phase in the form of a solution and in the heavy phase in the form of a precipitate are then measured:

TABLE 8

| | |
|---|---|
| Pongamol mass percentage light phase (supernatant) (%) | 5.58 |
| Pongamol mass percentage heavy phase (precipitate) (%) | 1.79 |
| Karanjin mass percentage light phase (supernatant) (%) | 3.18 |
| Karanjin mass percentage heavy phase (precipitate) (%) | 40.1 |
| $m_{pongamol}/m_{karanjin}$ ratio light phase (supernatant) | 1.75 |
| $m_{pongamol}/m_{karanjin}$ ratio heavy phase (precipitate) | 0.04 |

The light phase or supernatant is a solution consisting of approximately 50% of diethyl sebacate (CAS 110-40-7) and approximately 50% of extract of karanja oil enriched with pongamol.

The extraction yields are given below:

TABLE 9

| | |
|---|---|
| Pongamol extraction yield light phase (supernatant) (%) | 95.7 |
| Pongamol extraction yield heavy phase (precipitate) (%) | 4.3 |
| Karanjin extraction yield light phase (supernatant) (%) | 38.5 |
| Karanjin extraction yield heavy phase (precipitate) (%) | 61.5 |

In conclusion, using diethyl sebacate (CAS 110-40-7) at 50/50, one gets:
- an elimination of 61.5% of the karanjin of the light phase or supernatant in the form of a solution;
- a change in the $m_{pongamol}/m_{karanjin}$ ratio by a factor of 2.46 (1.75/0.71);
- an extraction yield of pongamol of 95.7%.

The light phase or supernatant in the form of a solution, once it has been separated from the heavy phase in the form of a precipitate, is a cosmetic ingredient according to the invention consisting of a solution comprising an extract of karanja oil and diethyl sebacate (CAS 110-40-7). This cosmetic ingredient/this solution can, for example, be incorporated directly in a cosmetic formulation, without elimination of the diethyl sebacate (CAS 110-40-7) and without a step of solubilization of pongamol.

This cosmetic ingredient consisting of a solution is characterized as follows:

TABLE 10

| Property | Result |
|---|---|
| Appearance | Red/orange oil |
| Color (Gardner scale) | <16 |
| Index of refraction (25° C.) | 1.504 |
| Density (20° C.; g/cm³) | 1.034 |
| Acid index (mg KOH/g) | 36.1 |
| Mass percentage pongamol (%) | 5.58 |
| Mass percentage karanjin (%) | 3.18 |
| Moisture content (K.F., %) | <0.1 |

Example 3: Precipitation Tests with Other Solvents According to the Invention

A molecular distillation of a karanja oil originating from another lot than the lot used in example 1 is carried out by means of an industrial thin-layer distiller, under the following conditions: distillation temperature 170° C., vacuum $10^{-2}$ mbar. The karanja oil which has been subjected to the molecular distillation is characterized as follows:

TABLE 11

| | |
|---|---|
| Acid index (mg KOH/g) | 67.0 |
| Mass percentage pongamol (%) | 2.65 |
| Mass percentage karanjin (%) | 15.5 |
| $m_{pongamol}/m_{karanjin}$ ratio | 0.17 |

The precipitation tests are then carried out on the karanja oil with different solvents:
- diethyl sebacate (CAS 110-40-7) (test 1);
- diisopropyl sebacate (CAS 7491-02-3) (test 2).

The mixture is stirred for 24 h at 15° C. A precipitate forms. The suspension is then filtered through an 11 μm filter.

The mass balances of the tests are given below:

TABLE 12

| | Test | |
|---|---|---|
| | 1 | 2 |
| Nature of the solvent | diethyl sebacate (CAS 110-40-7) | diisopropyl sebacate (CAS 7491-02-3) |
| Solvent/karanja oil mass percentage | 20/80 | 20/80 |
| Light phase (supernatant) (%) | 53.7 | 56.0 |
| Heavy phase (precipitate) (%) | 46.3 | 44.0 |

The mass balances are similar.

The pongamol and karanjin contents in the light phase in the form of a solution and in the heavy phase in the form of a precipitate are then measured:

TABLE 13

| | Test | |
|---|---|---|
| | 1 | 2 |
| Nature of the solvent | diethyl sebacate (CAS 110-40-7) | diisopropyl sebacate (CAS 7491-02-3) |
| Solvent/karanja oil mass percentage | 20/80 | 20/80 |
| Pongamol mass percentage light phase (supernatant) (%) | 2.67 | 2.51 |
| Pongamol mass percentage heavy phase (precipitate) (%) | 2.15 | 2.51 |
| Karanjin mass percentage light phase (supernatant) (%) | 0.72 | 4.19 |
| Karanjin mass percentage heavy phase (precipitate) (%) | 25.22 | 14.90 |
| $m_{pongamol}/m_{karanjin}$ ratio light phase (supernatant) | 3.70 | 0.60 |

The extraction yields are given below:

TABLE 14

| | Test | |
|---|---|---|
| | 1 | 2 |
| Nature of the solvent | diethyl sebacate (CAS 110-40-7) | diisopropyl sebacate (CAS 7491-02-3) |
| Solvent/karanja oil mass percentage | 20/80 | 20/80 |
| Pongamol extraction yield light phase (supernatant) (%) | 65.1 | 63.8 |
| Pongamol extraction yield heavy phase (precipitate) (%) | 34.9 | 36.2 |
| Karanjin extraction yield light phase (supernatant) (%) | 3.0 | 18.2 |
| Karanjin extraction yield heavy phase (precipitate) (%) | 97.0 | 81.8 |

In conclusion, using diethyl sebacate (CAS 110-40-7) at 20/80, one gets:
- an elimination of 97.0% of the karanjin of the light phase or supernatant in the form of a solution;
- a change in the $m_{pongamol}/m_{karanjin}$ ratio by a factor of 21.76 (3.70/0.17);
- an extraction yield of pongamol of 65.1%.

In conclusion, using diisopropyl sebacate (CAS 7491-02-3) at 20/80, one gets:
- an elimination of 81.8% of karanjin of the light phase or supernatant in the form of a solution;
- a change in the $m_{pongamol}/m_{karanjin}$ ratio by a factor of 3.53 (0.6/0.17);
- an extraction yield of pongamol of 63.8%.

Diethyl sebacate is thus superior to diisopropyl sebacate insofar as its capacity to precipitate karanjin is concerned, the extraction yield of pongamol being similar.

Here again, the light phase or supernatant in the form of a solution, once it has been separated from the heavy phase in the form of a precipitate, is a cosmetic ingredient according to the invention, consisting of a solution comprising an extract of karanja oil and a solvent (diethyl sebacate or diisopropyl sebacate). This cosmetic ingredient/this solution can, for example, be incorporated directly in a cosmetic formulation, without elimination of the solvent (diethyl sebacate or diisopropyl sebacate) and without a step of solubilization of pongamol.

Example 4: Precipitation Tests with Different Proportions of Diethyl Sebacate

A molecular distillation is carried out under the same conditions as those described in example 1, using another lot of karanja oil. At the end of the molecular distillation, the karanja oil is characterized as follows:

TABLE 15

| Acid index (mg KOH/g) | 67.0 |
| Pongamol mass percentage (%) | 3.25 |
| Karanjin mass percentage (%) | 11.4 |
| $m_{pongamol}/m_{karanjin}$ ratio | 0.28 |

Precipitation tests 1 to 8 are then carried out on the karanja oil with diethyl sebacate (CAS 110-40-7), according to different diethyl sebacate/karanja oil proportions.

The light phase or supernatant in the form of a solution and the heavy phase or precipitate are separated by centrifugation.

The mass balances of the tests are given below:

TABLE 16

| | Test | | | | | | | |
|---|---|---|---|---|---|---|---|---|
| | 1 | 2 | 3 | 4 | 5 | 6 | 7 | 8 |
| Mass % diethyl sebacate/ karanja oil | 84/ 16 | 80/ 20 | 71.5/ 28.5 | 62.5/ 37.5 | 50/ 50 | 40/ 60 | 25/ 75 | 20/ 80 |
| Light phase (supernatant) (%) | 95.6 | 97.3 | 94.5 | 90.6 | 84.5 | 75.1 | 61.6 | 63.1 |
| Heavy phase (precipitate) (%) | 4.4 | 2.7 | 5.5 | 9.4 | 15.5 | 24.9 | 38.4 | 36.9 |

The pongamol and karanjin contents in the light phase (supernatant) and in the heavy phase (precipitate) are then measured:

TABLE 17

| | Test | | | | | | | |
|---|---|---|---|---|---|---|---|---|
| | 1 | 2 | 3 | 4 | 5 | 6 | 7 | 8 |
| Mass % diethyl sebacate/ karanja oil | 84/ 16 | 80/ 20 | 71.5/ 28.5 | 62.5/ 37.5 | 50/ 50 | 40/ 60 | 25/ 75 | 20/ 80 |
| Mass percentage pongamol light phase (supernatant) (%) | 0.57 | 0.64 | 0.87 | 1.35 | 1.48 | 1.99 | 2.44 | 2.51 |
| Mass percentage pongamol heavy phase (precipitate) (%) | 0.68 | 0.67 | 0.80 | 1.01 | 1.43 | 1.71 | 2.24 | 2.41 |
| Mass percentage karanjin light phase (supernatant) (%) | 1.50 | 1.64 | 2.18 | 2.40 | 2.50 | 2.62 | 2.85 | 2.91 |
| Mass percentage karanjin heavy phase (precipitate) (%) | 13.42 | 8.91 | 23.74 | 19.28 | 21.67 | 17.39 | 14.80 | 15.20 |
| $m_{pongamol}/m_{karanjin}$ ratio light phase (supernatant) (%) | 0.38 | 0.39 | 0.40 | 0.56 | 0.59 | 0.76 | 0.86 | 0.86 |

The extraction yields are given below:

TABLE 18

| | Test | | | | | | | |
|---|---|---|---|---|---|---|---|---|
| | 1 | 2 | 3 | 4 | 5 | 6 | 7 | 8 |
| Mass % diethyl sebacate/ karanja oil | 84/ 16 | 80/ 20 | 71.5/ 28.5 | 62.5/ 37.5 | 50/ 50 | 40/ 60 | 25/ 75 | 20/ 80 |
| Extraction yield pongamol light phase (supernatant) (%) | 91.1 | 97.8 | 90.2 | 98.2 | 76.8 | 76.9 | 60.9 | 60.9 |
| Extraction yield pongamol heavy phase (precipitate) (%) | 8.9 | 2.2 | 9.8 | 1.8 | 23.2 | 23.1 | 39.1 | 39.1 |
| Extraction yield karanjin light phase (supernatant) (%) | 72.5 | 72.0 | 64.0 | 49.8 | 36.9 | 28.8 | 20.3 | 20.1 |
| Extraction yield karanjin heavy phase (precipitate) (%) | 27.5 | 28.0 | 36.0 | 50.2 | 63.1 | 71.2 | 79.7 | 79.1 |

Figure 3:
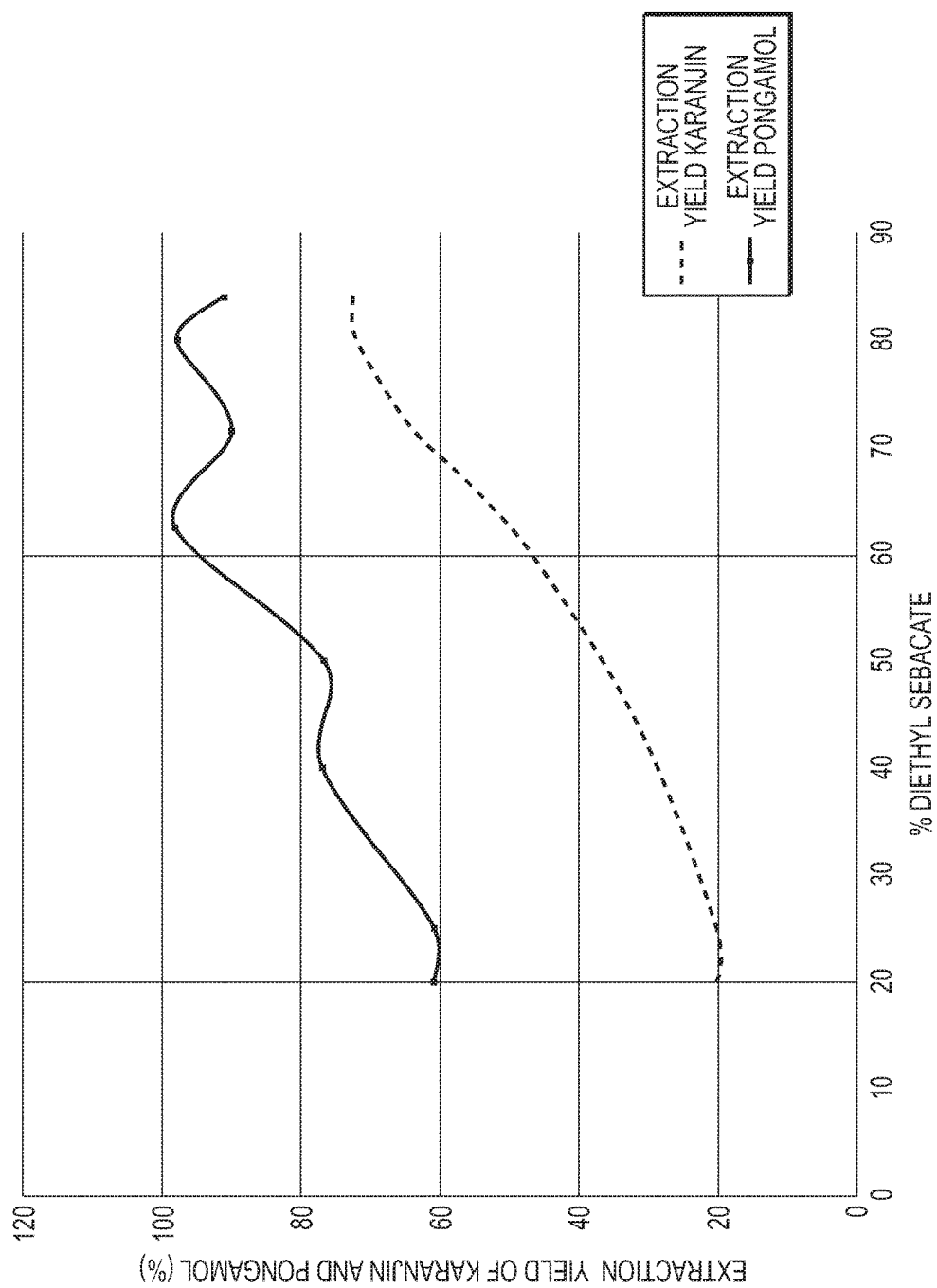
FIG. 3 is a curve representing the extraction yields of pongamol and karanjin in the light phase or supernatant in the form of a solution as a function of the diethyl sebacate proportion used.

A curve representing the extraction yields of pongamol and of karanjin in the light phase or supernatant in the form of a solution as a function of the diethyl sebacate proportion used is given in FIG. 3. FIG. 3 shows the change in the pongamol and karanjin extraction yields as a function of the diethyl sebacate proportion used.

As a function of the pongamol and karanjin mass percentages, the proportion of solvent has to be adjusted in order to obtain a karanjin mass percentage that is in compliance with the specifications and in order to obtain a $m_{pongamol}/m_{karanjin}$ ratio greater than or equal to 0.5.

Here again, in particular for tests 4-8, the light phase or supernatant in the form of a solution, once it has been separated from the heavy phase or precipitate, is a cosmetic ingredient according to the invention consisting of a solution comprising an extract of karanja oil and diethyl sebacate. This cosmetic ingredient/this solution can, for example, be incorporated directly in a cosmetic formulation, without removal of the diethyl sebacate and without a step of solubilization of the pongamol.

Example 5: Formulation Example According to the Invention

A formulation example according to the invention and an example of an operating procedure are given below:

TABLE 19

| Ingredient | % by weight | Supplier |
|---|---|---|
| Phase A | | |
| Light phase or supernatant in the form of a solution = cosmetic ingredient according to the invention (solvent: diethyl sebacate) | 7.5 | Biosynthis |
| Ethylhexyl salicylate | 5.0 | Symrise |
| Octocrylene (CAS 6197-30-4) | 2.0 | DSM |
| Avobenzone (CAS 70356-09-1) | 2.0 | DSM |
| Phase B | | |
| Caprylyl Methicone (CAS 17955-883) | 4.0 | Dow Corning |
| Coconut alkanes | 3.0 | Biosynthis |
| Trimethylsiloxysilicate (and) Polypropylsilsesquioxane | 3.0 | Dow Corning |
| PEG-12 Dimethicone (CAS 68937-54-2) | 4.0 | Dow Corning |
| Phase C | | |
| Decyl Glucoside | 0.5 | BASF |
| Glycerol | 5.0 | Oléon |
| Deionized water | 61.6 | / |
| Phase D | | |
| Polyacrylamide (and) C13-14 Isoparaffin (and) Laureth-7 | 2.0 | Seppic |
| Phase E | | |
| Butylparaben (CAS 94-26-8) | 0.4 | Pharmco-AAPER |

The cosmetic formulation is prepared according to the following operating procedure which comprises 9 steps:

1) In a separate mixer, mix all the components of phase A, under stirring at 60° C. and until the homogenization is complete;

2) Cool to ambient temperature under constant stirring;

3) In parallel, in a second mixer, mix the constituents of phase B until complete homogenization;

4) At ambient temperature, add phases A and B, until the homogenization is complete;

5) In a third mixer, mix the constituents of phase C;

6) Mix phases (A+B) and C under stirring;

7) Stir for 20 minutes at 1500 rotations/minute;

8) Mix (A+B+C)+D, until the homogenization is complete;

9) Add E to (A+B+C+D) while maintaining the stirring.

Example 6: Protective Properties of a Cosmetic Formulation According to the Invention (In Vivo)

A cosmetic ingredient according to the invention is produced according to the method presented in example 2; this cosmetic ingredient comprises approximately 50% of diethyl sebacate (supplied by ARKEMA) and approximately 50% of extract of karanja oil enriched with pongamol.

The cosmetic ingredient according to the invention is then formulated; the cosmetic formulation according to the invention has the following qualitative and quantitative compositions:

TABLE 20

| Components | % by weight | Supplier |
|---|---|---|
| cosmetic ingredient according to the invention (solvent: diethyl sebacate, approximately 50%) | 65 | BIOSYNTHIS |
| Coconut oil gel 35 (INCI: Coconut oil and dilinoleic acid/Propanediol/Octyldodecanol copolymer) | 30 | BIOSYNTHIS |
| Trihydroxystearin (CAS 139-44-6) | 5 | BASF/Cognis |

The Sun Protection Factor (SPF) was determined for the cosmetic formulation according to the invention according to the recommendations of the International Standard ISO 24444 (November 2010) using a panel of three subjects.

The results obtained are presented in the table below:

TABLE 21

| Subject | Age | ITA° | Photo-type | MED up | MED p | iSPF formulation tested | iSPF standard product P2 |
|---|---|---|---|---|---|---|---|
| Subject 1 | 54 | 50.7 | II | 31.1 | 1642.6 | 52.9 | 16.0 |
| Subject 2 | 26 | 41.1 | III | 32.0 | 1946.7 | 60.8 | 16.0 |
| Subject 3 | 48 | 52.6 | II | 26.0 | 1581.7 | 60.8 | 16.0 |
| Mean | | | | | | 58.2 | 16.0 |
| Standard deviation | | | | | | 4.6 | 0.0 |

MEDup: Minimal Erythemal Dose of the unprotected skin
MEDp: Minimal Erythemal Dose of the protected skin
iSPF: Individual Sun Protection Factor
ITA: Individual Typology Angle The cosmetic formulation according to the invention has a mean SPF equal to 58.2, which corresponds to a high degree of sun protection.

The good sunscreen properties of the cosmetic formulation according to the invention are thus confirmed in vivo.

Example 7: Protective Properties of a Cosmetic Ingredient According to the Invention (In Vitro)

A cosmetic ingredient according to the invention is prepared according to the method presented in example 2; this cosmetic ingredient comprises approximately 50% of diethyl sebacate and approximately 50% of extract of karanja oil enriched with pongamol.

For the cosmetic ingredient according to the invention and for a deodorized karanja oil, the Sun Protection Factor was determined by means of PMMA plates according to the method described in the publication Pissavini et al., "Determination of the in vitro FPS," Cosmetics and toiletries, 2003, vol. 118, No. 10, pp. 63-72.

The results obtained are presented in the table below:

TABLE 22

| Composition | Mass percentage of pongamol (%) | SPF/ SPF IR | UVA protection/ UVA IR protection |
|---|---|---|---|
| Deodorized Karanja oil | 1.4 | 18.2/12.7 | 9.9/7.8 |
| Cosmetic ingredient according to the invention | 7.7 | 190/174 | 76/72 |
| PMMA control | NA | 25.7 | 9.0 |

SPF: Sun Protection Factor
IR: after irradiation
SPF IR: Sun Protection Factor after irradiation The cosmetic ingredient according to the invention has a very high SPF compared to that of the deodorized Karanja oil.

The good sunscreen properties of the cosmetic ingredient according to the invention are thus confirmed in vitro.

One notes that the cosmetic ingredient according to the invention has an SPF increased by a factor of more than 10, and a UVA protection which is also increased by a factor close to 10.

Also, the irradiation of the cosmetic ingredient according to the invention has relatively little influence on the SPF (from 190 to 174, the SPF is decreased by approximately 9%) and on the UVA protection (from 76 to 72, the UVA protection is decreased by approximately 5%), while the irradiation of the deodorized karanja oil has much influence on the SPF (from 18.2 to 12.7, the SPF is decreased by approximately 30%) and on the UVA protection (from 9.9 to 7.8, the UVA protection is decreased by approximately 20%).

The invention claimed is:

1. A cosmetic ingredient, that consists of a solution of at least one extract of karanja oil comprising pongamol (CAS 484-33-3) and karanjin (CAS 521-88-0) in at least one solvent selected from the group of compounds having the following formula (I), or mixtures thereof:

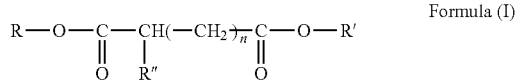

Formula (I)

in which:
n is from 0 to 19;
R and R', which may be identical or different, are alkyls derived from an esterification by a linear or branched alcohol of molecular formula $C_xH_{2x+2}O$, x being from 1 to 30,
R" is either a hydrogen atom or a $C_1$-$C_3$ alkyl group.

2. The cosmetic ingredient according to claim 1, wherein at least one solvent is selected from the group consisting of the sebacates (n=7), the adipates (n=3), the succinates (n=1), the dodecanedioates (n=9), the azelates (n=6), the glutarates (n=2), the malonates (n=0), and mixtures thereof.

3. The cosmetic ingredient according to claim 1, wherein at least one solvent is selected from the group consisting of the sebacates (n=7).

4. The cosmetic ingredient according claim 1, wherein at least one solvent is diethyl sebacate (CAS 110-40-7).

5. The cosmetic ingredient according to claim 1, wherein the mass percentage of said at least one solvent in said solution is from 20% to 60%.

6. The cosmetic ingredient according to claim 1, wherein the mass percentage of pongamol in said solution is greater than 1.30%.

7. The cosmetic ingredient according to claim 1, wherein the mass percentage of karanjin in said solution is less than 6%.

8. The cosmetic ingredient according to claim 1, wherein the $m_{pongamol}/m_{karanjin}$ ratio in said solution is greater than 0.5.

9. A cosmetic formulation, wherein:
at least one cosmetic ingredient according to claim 1 and
at least one cosmetically acceptable vehicle.

10. A method comprising applying a solar cosmetic formulation and/or as an anti-aging cosmetic formulation as a cosmetic formulation according to claim 9.

11. A process of selective precipitation of pongamol (CAS 484-33-3) in a karanja oil comprising pongamol (CAS 484-33-3) and karanjin (CAS 521-88-0), wherein:
1) at least one step of addition to said at least one karanja oil of at least one solvent selected from the group of the diesters having the following formula (I), or mixtures thereof:

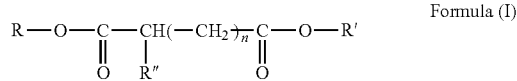

Formula (I)

in which:
n is from 0 to 19;
R and R', which may be identical or different, are alkyls derived from an esterification by a linear or branched alcohol of molecular formula $C_xH_{2x+2}O$, x being from 1 from 30,
R" is either a hydrogen atom or a $C_1$-$C_3$ alkyl group;
said addition having the effect of forming a light phase in the form of a solution and a heavy phase in the form of a precipitate; and
2) at least one step of separation of the two phases obtained.

12. The process according to claim 11, wherein at least one solvent is selected from the group consisting of the sebacates (n=7), the adipates (n=3), the succinates (n=1), the dodecanedioates (n=9), the azelates (n=6), the glutarates (n=2), the malonates (n=0), and mixtures thereof.

13. The process according to claim 11, wherein at least one solvent is selected from the group consisting of the sebacates (n=7).

14. The process according to claim 11, wherein at least one solvent is diethyl sebacate (CAS 110-40-7).

15. The process according to claim 11, wherein in said step 1), the mass proportion of said at least one solvent introduced into said at least one karanja oil is from 60/40 to 20/80.

16. The process according to claim 11, wherein it includes, in addition, at least one preliminary step of deodorization of said at least one karanja oil and/or at least one preliminary step of distillation of said at least one karanja oil, said steps, when they are both present, being capable of being carried out in any order.

* * * * *